United States Patent
Müller et al.

(10) Patent No.: US 10,048,284 B2
(45) Date of Patent: Aug. 14, 2018

(54) SAMPLE CONTAINER CAP WITH CENTRIFUGATION STATUS INDICATOR DEVICE

(71) Applicant: Beckman Coulter, Inc., Brea, CA (US)

(72) Inventors: Martin Müller, Schliersee-Neuhaus (DE); Andreas Weihs, Landsberg (DE); Gerhard Gunzer, Reinheim (DE); Michael Eberhardt, München (DE)

(73) Assignee: Beckman Coulter, Inc., Brea, CA (US)

( * ) Notice: Subject to any disclaimer, the term of this patent is extended or adjusted under 35 U.S.C. 154(b) by 281 days.

(21) Appl. No.: 14/699,734

(22) Filed: Apr. 29, 2015

(65) Prior Publication Data

US 2015/0238978 A1 Aug. 27, 2015

Related U.S. Application Data

(62) Division of application No. 13/671,454, filed on Nov. 7, 2012, now Pat. No. 9,046,506.
(Continued)

(51) Int. Cl.
*G01N 35/00* (2006.01)
*B65G 47/28* (2006.01)
(Continued)

(52) U.S. Cl.
CPC ....... *G01N 35/0099* (2013.01); *B01D 21/262* (2013.01); *B04B 7/02* (2013.01);
(Continued)

(58) Field of Classification Search
CPC .............. G01N 35/1009; G01N 35/10; G01N 35/00732; G01N 35/0099; G01N 35/04;
(Continued)

(56) References Cited

U.S. PATENT DOCUMENTS 3,158,765 A 11/1964 Prolgreen
4,052,161 A 10/1977 Atwood et al.
(Continued)

FOREIGN PATENT DOCUMENTS

CA 1 282 692 A1 4/1991
CN 1127887 A 7/1996
(Continued)

OTHER PUBLICATIONS

First Chinese Office Action dated Jun. 23, 2015 for CN Patent Application No. 201280066162.4, with English Translation, 18 pages.
(Continued)

*Primary Examiner* — Walter D Griffin
*Assistant Examiner* — Shuyi S Liu
(74) *Attorney, Agent, or Firm* — Kilpatrick Townsend & Stockton LLP

(57) ABSTRACT

A sample container cap is disclosed. The sample cap container includes a sample cap body capable of covering an opening of a sample container and a centrifugation status indicator device in the top of the sample cap body. The centrifugation status indicator device includes: a first substance having a first density and a first color, and a second substance having a second density and a second color. The centrifugation status indicator device displays the first substance when the sample container has been centrifuged. The first substance can be a gel, and the second substance can include a plurality of particles. The second density is higher than the first density and the second color is different from the first color.

17 Claims, 12 Drawing Sheets

ROTATED TO EMERGENCY POSITION

Related U.S. Application Data

(60) Provisional application No. 61/556,667, filed on Nov. 7, 2011, provisional application No. 61/616,994, filed on Mar. 28, 2012, provisional application No. 61/680,066, filed on Aug. 6, 2012.

(51) Int. Cl.

| | | |
|---|---|---|
| *B01D 21/26* | (2006.01) | |
| *B04B 7/08* | (2006.01) | |
| *B04B 15/00* | (2006.01) | |
| *B25J 11/00* | (2006.01) | |
| *B04B 9/14* | (2006.01) | |
| *G01N 35/04* | (2006.01) | |
| *G01B 11/02* | (2006.01) | |
| *G01B 11/08* | (2006.01) | |
| *G01B 11/10* | (2006.01) | |
| *G01M 1/14* | (2006.01) | |
| *G01N 21/27* | (2006.01) | |
| *G01N 35/10* | (2006.01) | |
| *B04B 7/02* | (2006.01) | |
| *B04B 13/00* | (2006.01) | |
| *B65D 51/24* | (2006.01) | |
| *G01L 19/08* | (2006.01) | |
| *B04B 11/04* | (2006.01) | |
| *G01B 11/24* | (2006.01) | |
| *G01F 23/00* | (2006.01) | |
| *B01L 3/00* | (2006.01) | |

(52) U.S. Cl.
CPC ............... *B04B 7/08* (2013.01); *B04B 9/14* (2013.01); *B04B 9/146* (2013.01); *B04B 11/04* (2013.01); *B04B 13/00* (2013.01); *B04B 15/00* (2013.01); *B25J 11/00* (2013.01); *B65D 51/24* (2013.01); *B65G 47/28* (2013.01); *G01B 11/02* (2013.01); *G01B 11/08* (2013.01); *G01B 11/10* (2013.01); *G01B 11/24* (2013.01); *G01F 23/00* (2013.01); *G01L 19/08* (2013.01); *G01M 1/14* (2013.01); *G01N 21/27* (2013.01); *G01N 35/00584* (2013.01); *G01N 35/00732* (2013.01); *G01N 35/04* (2013.01); *G01N 35/10* (2013.01); *G01N 35/1009* (2013.01); *B01L 3/5021* (2013.01); *B04B 2009/143* (2013.01); *B04B 2011/046* (2013.01); *B04B 2013/006* (2013.01); *G01N 2035/00495* (2013.01); *G01N 2035/0405* (2013.01); *G01N 2035/0462* (2013.01); *G01N 2035/0491* (2013.01); *G01N 2035/1025* (2013.01); *G01N 2035/1032* (2013.01); *Y10T 29/49826* (2015.01)

(58) Field of Classification Search
CPC ........... G01N 21/27; G01N 2035/1025; G01N 2035/0491; G01N 2035/1032; G01N 2035/0462; G01N 2035/0405; G01N 2035/00495; G01L 19/08; B65D 51/24; B04B 13/00; B04B 7/02; B04B 7/08; B04B 15/00; B04B 9/146; B04B 2013/006; B04B 2011/046; B65G 47/28; G01M 1/14; B01D 21/262; B25J 11/00; Y10T 29/49826; B01L 3/5021; G01B 11/02; G01B 11/08; G01B 11/10
USPC ............... 494/10, 16, 20; 206/459.1
See application file for complete search history.

(56) References Cited

U.S. PATENT DOCUMENTS

| | | |
|---|---|---|
| 4,101,070 A | 7/1978 | Hoare et al. |
| 4,119,381 A | 10/1978 | Muka et al. |
| 4,250,266 A | 2/1981 | Wade |
| 4,401,189 A | 8/1983 | Majewski |
| 4,486,539 A | 12/1984 | Ranki et al. |
| 4,501,495 A | 2/1985 | Faulkner et al. |
| 4,530,056 A | 7/1985 | MacKinnon et al. |
| 4,588,556 A | 5/1986 | Sarstedt |
| 4,593,238 A | 6/1986 | Yamamoto |
| 4,593,239 A | 6/1986 | Yamamoto |
| 4,673,657 A | 6/1987 | Christian |
| 4,674,640 A | 6/1987 | Asa et al. |
| 4,676,952 A | 6/1987 | Edelmann et al. |
| 4,683,195 A | 7/1987 | Mullis et al. |
| 4,683,202 A | 7/1987 | Mullis |
| 4,751,177 A | 6/1988 | Stabinsky |
| 4,780,817 A | 10/1988 | Lofgren |
| 4,800,159 A | 1/1989 | Mullis et al. |
| 4,851,330 A | 7/1989 | Kohne |
| 4,865,986 A | 9/1989 | Coy et al. |
| 4,943,415 A | 7/1990 | Przybylowicz et al. |
| 4,947,094 A | 8/1990 | Dyer et al. |
| 4,950,613 A | 8/1990 | Arnold, Jr. et al. |
| 5,055,393 A | 10/1991 | Kwoh et al. |
| 5,055,408 A | 10/1991 | Higo et al. |
| 5,075,853 A | 12/1991 | Luke, Jr. |
| 5,102,518 A | 4/1992 | Doering et al. |
| 5,118,191 A | 6/1992 | Hopkins |
| 5,147,529 A | 9/1992 | Lee et al. |
| 5,154,888 A | 10/1992 | Zander et al. |
| 5,158,895 A | 10/1992 | Ashihara et al. |
| 5,168,766 A | 12/1992 | Henschke et al. |
| 5,179,329 A | 1/1993 | Nishikawa et al. |
| 5,185,439 A | 2/1993 | Arnold, Jr. et al. |
| 5,186,827 A | 2/1993 | Liberti et al. |
| 5,190,136 A | 3/1993 | Grecksch et al. |
| 5,196,168 A | 3/1993 | Muszak et al. |
| 5,205,393 A | 4/1993 | Malow et al. |
| 5,229,297 A | 7/1993 | Schinpelsky et al. |
| 5,234,665 A | 8/1993 | Ohta et al. |
| 5,244,055 A | 9/1993 | Shimizu |
| 5,283,174 A | 2/1994 | Arnold et al. |
| 5,283,739 A | 2/1994 | Summerville et al. |
| 5,288,463 A | 2/1994 | Chemelli |
| 5,330,916 A | 7/1994 | Williams et al. |
| 5,350,564 A | 9/1994 | Mazza et al. |
| 5,351,801 A | 10/1994 | Markin et al. |
| 5,362,291 A | 11/1994 | Williamson, IV |
| 5,366,896 A | 11/1994 | Ooura et al. |
| 5,374,395 A | 12/1994 | Robinson et al. |
| 5,375,898 A | 12/1994 | Ohmori et al. |
| 5,380,487 A | 1/1995 | Choperena et al. |
| 5,388,682 A | 2/1995 | Dudley |
| 5,389,339 A | 2/1995 | Petschek et al. |
| 5,397,709 A | 3/1995 | Berndt |
| 5,399,491 A | 3/1995 | Kacian et al. |
| 5,403,711 A | 4/1995 | Walder et al. |
| 5,415,839 A | 5/1995 | Zuan et al. |
| 5,422,271 A | 6/1995 | Chen et al. |
| 5,427,930 A | 6/1995 | Birkenmeyer et al. |
| 5,437,990 A | 8/1995 | Burg et al. |
| 5,443,791 A | 8/1995 | Cathcart et al. |
| 5,447,687 A | 9/1995 | Lewis et al. |
| 5,449,602 A | 9/1995 | Royer et al. |
| 5,462,881 A | 10/1995 | Perlman |
| 5,466,574 A | 11/1995 | Liberti et al. |
| 5,480,784 A | 1/1996 | Kacian et al. |
| 5,482,834 A | 1/1996 | Gillespie |
| 5,504,345 A | 4/1996 | Bartunek et al. |
| 5,514,550 A | 5/1996 | Findlay et al. |
| 5,525,300 A | 6/1996 | Danssaert et al. |
| 5,527,673 A | 6/1996 | Reinhartz et al. |
| 5,536,649 A | 7/1996 | Fraiser et al. |
| 5,538,849 A | 7/1996 | Uematsu et al. |
| 5,554,516 A | 9/1996 | Kacian et al. |

(56) References Cited

U.S. PATENT DOCUMENTS

| | | |
|---|---|---|
| 5,563,037 A | 10/1996 | Sutherland et al. |
| 5,578,270 A | 11/1996 | Reichler et al. |
| 5,582,796 A | 12/1996 | Carey et al. |
| 5,585,242 A | 12/1996 | Bourma et al. |
| 5,585,481 A | 12/1996 | Arnold, Jr. et al. |
| 5,587,128 A | 12/1996 | Wilding et al. |
| 5,589,333 A | 12/1996 | Bagasra et al. |
| 5,602,042 A | 2/1997 | Farber |
| 5,604,130 A | 2/1997 | Warner et al. |
| 5,612,200 A | 3/1997 | Dattagupta et al. |
| 5,612,525 A | 3/1997 | Apter et al. |
| 5,623,415 A | 4/1997 | O'Bryan et al. |
| 5,628,962 A | 5/1997 | Kanbara et al. |
| 5,637,275 A | 6/1997 | Carey et al. |
| 5,639,599 A | 6/1997 | Ryder |
| 5,639,604 A | 6/1997 | Arnold et al. |
| 5,641,658 A | 6/1997 | Adams et al. |
| 5,652,489 A | 7/1997 | Kawakami |
| 5,653,940 A | 8/1997 | Carey et al. |
| 5,656,493 A | 8/1997 | Mullis et al. |
| 5,665,554 A | 9/1997 | Reeve et al. |
| 5,679,553 A | 10/1997 | Van Gemen et al. |
| 5,686,272 A | 11/1997 | Marshall et al. |
| 5,702,950 A | 12/1997 | Tajima |
| 5,705,062 A | 1/1998 | Knobel |
| 5,714,380 A | 2/1998 | Neri et al. |
| 5,720,923 A | 2/1998 | Haff et al. |
| 5,723,591 A | 3/1998 | Livak et al. |
| 5,730,938 A | 3/1998 | Carbonari et al. |
| 5,735,587 A | 4/1998 | Malin et al. |
| 5,741,708 A | 4/1998 | Carey et al. |
| 5,746,978 A | 5/1998 | Bienhaus et al. |
| 5,750,338 A | 5/1998 | Collins et al. |
| 5,773,268 A | 6/1998 | Korenberg et al. |
| 5,779,981 A | 7/1998 | Danssaert et al. |
| 5,786,182 A | 7/1998 | Catanzariti et al. |
| 5,795,547 A | 8/1998 | Moser et al. |
| 5,798,263 A | 8/1998 | Wood et al. |
| 5,814,008 A | 9/1998 | Chen et al. |
| 5,814,276 A | 9/1998 | Riggs |
| 5,814,961 A | 9/1998 | Imahashi |
| 5,827,653 A | 10/1998 | Sammes et al. |
| 5,846,489 A | 12/1998 | Bienhaus et al. |
| 5,846,491 A | 12/1998 | Choperena et al. |
| 5,846,726 A | 12/1998 | Nadeau et al. |
| 5,857,955 A | 1/1999 | Phillips et al. |
| 5,866,336 A | 2/1999 | Nazarenko et al. |
| 5,881,781 A | 3/1999 | Bishop |
| 5,882,903 A | 3/1999 | Andrevski et al. |
| 5,895,631 A | 4/1999 | Tajima et al. |
| 5,897,090 A | 4/1999 | Smith et al. |
| 5,897,783 A | 4/1999 | Howe et al. |
| 5,914,230 A | 6/1999 | Liu et al. |
| 5,919,622 A | 7/1999 | Macho et al. |
| 5,922,591 A | 7/1999 | Anderson et al. |
| 5,925,517 A | 7/1999 | Tyagi et al. |
| 5,928,907 A | 7/1999 | Woudenberg |
| 5,948,673 A | 9/1999 | Cottingham et al. |
| 5,966,309 A | 10/1999 | O'Bryan et al. |
| 5,994,056 A | 11/1999 | Higuchi et al. |
| 6,011,508 A | 1/2000 | Perreault et al. |
| 6,033,574 A | 3/2000 | Siddiqi |
| 6,033,880 A | 3/2000 | Haff et al. |
| 6,043,880 A | 3/2000 | Andrews et al. |
| 6,049,745 A | 4/2000 | Douglas et al. |
| 6,056,106 A | 5/2000 | van Dyke, Jr. et al. |
| 6,060,022 A | 5/2000 | Pang et al. |
| 6,063,340 A | 5/2000 | Lewis et al. |
| 6,068,978 A | 5/2000 | Zaun et al. |
| 6,071,395 A | 6/2000 | Lange |
| 6,100,079 A | 8/2000 | Tajima |
| 6,110,676 A | 8/2000 | Coull et al. |
| 6,110,678 A | 8/2000 | Weisburg et al. |
| 6,117,398 A | 9/2000 | Bienhaus et al. |
| 6,129,428 A | 10/2000 | Helwig et al. |
| 6,150,097 A | 11/2000 | Tyagi et al. |
| 6,165,778 A | 12/2000 | Kedar |
| 6,171,780 B1 | 1/2001 | Pham et al. |
| 6,212,448 B1 | 4/2001 | Xydis |
| 6,277,332 B1 | 8/2001 | Sucholeiki |
| 6,300,068 B1 | 10/2001 | Burg et al. |
| 6,300,138 B1 | 10/2001 | Gleason et al. |
| 6,306,658 B1 | 10/2001 | Turner et al. |
| 6,333,008 B1 | 12/2001 | Leistner et al. |
| 6,335,166 B1 | 1/2002 | Ammann et al. |
| 6,353,774 B1 | 3/2002 | Goldenberg et al. |
| 6,368,872 B1 | 4/2002 | Juranas |
| 6,370,452 B1 | 4/2002 | Pfister |
| 6,374,989 B1 | 4/2002 | van Dyke, Jr. et al. |
| 6,377,888 B1 | 4/2002 | Olch |
| 6,429,016 B1 | 8/2002 | McNeil |
| 6,436,349 B1 | 8/2002 | Carey et al. |
| 6,444,171 B1 | 9/2002 | Sakazume et al. |
| RE37,891 E | 10/2002 | Collins et al. |
| 6,458,324 B1 | 10/2002 | Schinzel |
| 6,520,313 B1 | 2/2003 | Kaarakainen et al. |
| 6,548,026 B1 | 4/2003 | Dales et al. |
| 6,586,234 B1 | 7/2003 | Burg et al. |
| 6,586,255 B1 | 7/2003 | Tanaka et al. |
| 6,597,450 B1 | 7/2003 | Andrews et al. |
| 6,599,476 B1 | 7/2003 | Watson et al. |
| 6,605,213 B1 | 8/2003 | Ammann et al. |
| 6,629,028 B2 | 9/2003 | Paromtchik et al. |
| 6,633,785 B1 | 10/2003 | Kasahara et al. |
| 6,692,708 B2 | 2/2004 | Chandler, Jr. |
| 6,719,896 B1 | 4/2004 | Clark |
| 6,764,649 B2 | 7/2004 | Ammann |
| 6,770,883 B2 | 8/2004 | McNeal et al. |
| 6,818,183 B2 | 11/2004 | Hajduk et al. |
| 6,890,742 B2 | 5/2005 | Ammann et al. |
| 6,919,058 B2 | 7/2005 | Andersson et al. |
| 6,919,175 B1 | 7/2005 | Beinhaus et al. |
| 6,941,200 B2 | 9/2005 | Sonoyama et al. |
| 6,993,176 B2 | 1/2006 | Yamagishi et al. |
| 7,028,831 B2 | 1/2006 | Veiner |
| 6,999,847 B2 | 2/2006 | Barry et al. |
| 7,033,820 B2 | 4/2006 | Ammann et al. |
| 7,045,358 B2 | 5/2006 | Chandler, Jr. |
| 7,071,006 B2 | 7/2006 | Tajima et al. |
| 7,078,698 B2 | 7/2006 | Itoh |
| 7,118,892 B2 | 10/2006 | Ammann et al. |
| 7,135,145 B2 | 11/2006 | Ammann et al. |
| 7,174,836 B2 | 2/2007 | Marino et al. |
| 7,237,749 B2 | 9/2007 | Wittwer et al. |
| 7,264,111 B2 | 9/2007 | Veiner |
| 7,267,795 B2 | 9/2007 | Ammann et al. |
| 7,269,480 B2 | 9/2007 | Hashimoto et al. |
| 7,288,229 B2 | 10/2007 | Turner et al. |
| 7,362,258 B2 | 4/2008 | Kawabe et al. |
| 7,419,830 B2 | 9/2008 | Canos et al. |
| 7,463,948 B2 | 12/2008 | Orita |
| 7,473,897 B2 | 1/2009 | Braendle et al. |
| 7,482,143 B2 | 1/2009 | Ammann et al. |
| 7,499,581 B2 | 3/2009 | Tribble et al. |
| 7,524,652 B2 | 4/2009 | Ammann et al. |
| 7,560,255 B2 | 7/2009 | Ammann et al. |
| 7,560,256 B2 | 7/2009 | Ammann et al. |
| 7,688,448 B2 | 3/2010 | Bamberg et al. |
| 7,771,659 B2 | 8/2010 | Ziegler |
| 8,074,578 B2 | 12/2011 | Thornton |
| 8,192,992 B2 | 6/2012 | Ammann et al. |
| 2002/0025064 A1 | 2/2002 | Itoh |
| 2002/0028489 A1 | 3/2002 | Ammann et al. |
| 2002/0031768 A1 | 3/2002 | McMillan et al. |
| 2002/0077239 A1 | 6/2002 | Evans, III et al. |
| 2002/0086417 A1 | 7/2002 | Chen |
| 2002/0098117 A1 | 7/2002 | Ammann et al. |
| 2002/0123156 A1 | 9/2002 | Tajima |
| 2002/0137194 A1 | 9/2002 | Ammann et al. |
| 2002/0137197 A1 | 9/2002 | Ammann et al. |
| 2002/0146347 A1 | 10/2002 | McNeil |
| 2002/0147515 A1 | 10/2002 | Fava et al. |
| 2003/0026736 A1 | 2/2003 | Hajduk et al. |
| 2003/0027206 A1 | 2/2003 | Ammann et al. |

(56) References Cited

U.S. PATENT DOCUMENTS

| | | |
|---|---|---|
| 2003/0029916 A1 | 2/2003 | Merva et al. |
| 2003/0054542 A1 | 3/2003 | Burns et al. |
| 2003/0129614 A1 | 7/2003 | Parameswaran et al. |
| 2003/0190755 A1 | 10/2003 | Turner et al. |
| 2003/0213313 A1 | 11/2003 | Katagi |
| 2003/0223916 A1 | 12/2003 | Testrut et al. |
| 2004/0029260 A1 | 2/2004 | Hansen et al. |
| 2004/0076983 A1 | 4/2004 | Karlsen |
| 2004/0086173 A1 | 5/2004 | Itoh |
| 2004/0087426 A1 | 5/2004 | Lattanzi |
| 2004/0115796 A1 | 6/2004 | Burns |
| 2004/0158355 A1 | 8/2004 | Holmqvist et al. |
| 2004/0184959 A1 | 9/2004 | Itoh |
| 2004/0206419 A1 | 10/2004 | Ganz et al. |
| 2004/0213651 A1 | 10/2004 | Malin |
| 2004/0265173 A1 | 12/2004 | Matsumoto et al. |
| 2005/0130198 A1 | 6/2005 | Ammann et al. |
| 2005/0158212 A1 | 7/2005 | Yavilevich |
| 2005/0163354 A1 | 7/2005 | Ziegler |
| 2005/0207937 A1 | 9/2005 | Itoh |
| 2005/0220670 A1 | 10/2005 | Palmieri et al. |
| 2005/0233370 A1 | 10/2005 | Ammann et al. |
| 2005/0239127 A1 | 10/2005 | Ammann et al. |
| 2005/0266489 A1 | 12/2005 | Ammann et al. |
| 2005/0271555 A1 | 12/2005 | Itoh |
| 2006/0003373 A1 | 1/2006 | Ammann et al. |
| 2006/0014295 A1 | 1/2006 | Ziegler |
| 2006/0020370 A1 | 1/2006 | Abramson |
| 2006/0148063 A1 | 7/2006 | Fauzzi et al. |
| 2006/0228268 A1 | 10/2006 | Heimberg et al. |
| 2007/0044676 A1 | 3/2007 | Clark et al. |
| 2007/0059209 A1 | 3/2007 | Pang et al. |
| 2007/0100498 A1 | 5/2007 | Matsumoto et al. |
| 2007/0110634 A1 | 5/2007 | Heimberg et al. |
| 2007/0134131 A1 | 6/2007 | Watson et al. |
| 2007/0179690 A1 | 8/2007 | Stewart |
| 2007/0184548 A1 | 8/2007 | Tan et al. |
| 2007/0193859 A1 | 8/2007 | Kyuyoku et al. |
| 2007/0196237 A1 | 8/2007 | Neuzil et al. |
| 2007/0208440 A1 | 9/2007 | Bliss et al. |
| 2007/0225901 A1 | 9/2007 | Yamaguchi |
| 2007/0225906 A1 | 9/2007 | Ikeda |
| 2008/0014181 A1 | 1/2008 | Ariff et al. |
| 2008/0015470 A1 | 1/2008 | Sarstedt |
| 2008/0056958 A1 | 3/2008 | Vijay et al. |
| 2008/0069730 A1 | 3/2008 | Itoh |
| 2008/0138249 A1 | 6/2008 | Itoh |
| 2008/0167817 A1 | 7/2008 | Hessler et al. |
| 2008/0241837 A1 | 10/2008 | Ammann et al. |
| 2008/0255683 A1 | 10/2008 | Takahashi et al. |
| 2008/0268528 A1 | 10/2008 | Ammann et al. |
| 2008/0274511 A1 | 11/2008 | Tan et al. |
| 2008/0297769 A1 | 12/2008 | Bamberg et al. |
| 2009/0029352 A1 | 1/2009 | Ammann et al. |
| 2009/0029871 A1 | 1/2009 | Ammann et al. |
| 2009/0029877 A1 | 1/2009 | Ammann et al. |
| 2009/0030551 A1 | 1/2009 | Hein et al. |
| 2009/0035185 A1 | 2/2009 | Tsujimura et al. |
| 2009/0042281 A1 | 2/2009 | Chang et al. |
| 2009/0047179 A1 | 2/2009 | Ping et al. |
| 2009/0117620 A1 | 5/2009 | Fritchie et al. |
| 2009/0232704 A1 | 9/2009 | Dohmae et al. |
| 2009/0318276 A1 | 12/2009 | Miler |
| 2009/0324032 A1 | 12/2009 | Chen |
| 2010/0018330 A1 | 1/2010 | Marty et al. |
| 2010/0028124 A1 | 2/2010 | Lackner et al. |
| 2010/0028203 A1 | 2/2010 | Frey et al. |
| 2010/0049358 A1 | 2/2010 | Koch et al. |
| 2010/0066996 A1 | 3/2010 | Kosaka et al. |
| 2010/0115887 A1 | 5/2010 | Schroeder et al. |
| 2010/0129789 A1 | 5/2010 | Self et al. |
| 2010/0141756 A1 | 6/2010 | Grote et al. |
| 2010/0219968 A1 | 9/2010 | Teutenberg |
| 2010/0261595 A1 | 10/2010 | Schaefer et al. |
| 2010/0291619 A1 | 11/2010 | Robinson et al. |
| 2011/0032621 A1* | 2/2011 | Marchand ............ C08F 297/083 359/586 |
| 2011/0065193 A1 | 3/2011 | Kitagawa et al. |
| 2011/0226584 A1 | 9/2011 | Ek |
| 2011/0311416 A1* | 12/2011 | Palmer .................. B01L 3/5453 422/547 |
| 2011/0313684 A1* | 12/2011 | Furrer .................. B01L 3/5021 702/41 |
| 2012/0129673 A1 | 5/2012 | Fukugaki et al. |
| 2012/0258463 A1 | 10/2012 | Duffy et al. |
| 2013/0123089 A1 | 5/2013 | Johns et al. |
| 2013/0125675 A1 | 5/2013 | Mueller et al. |
| 2013/0126302 A1 | 5/2013 | Johns et al. |
| 2013/0128035 A1 | 5/2013 | Johns et al. |
| 2013/0129166 A1 | 5/2013 | Mueller et al. |
| 2014/0037420 A1 | 2/2014 | Frey et al. |

FOREIGN PATENT DOCUMENTS

| | | |
|---|---|---|
| CN | 1164894 A | 11/1997 |
| CN | 1212019 A | 3/1999 |
| CN | 1212021 A | 3/1999 |
| CN | 1245218 A | 2/2000 |
| CN | 1281462 A | 1/2001 |
| CN | 1974781 A | 6/2007 |
| CN | 1010762859 A | 11/2007 |
| DE | 35 10 797 C2 | 1/1988 |
| DE | 696 33 532 T2 | 2/2006 |
| EP | 0 324 616 A2 | 7/1989 |
| EP | 0 328 829 A2 | 8/1989 |
| EP | 0 410 645 A2 | 1/1991 |
| EP | 0 479 448 A2 | 4/1992 |
| EP | 0 502 589 A2 | 9/1992 |
| EP | 0 502 638 A2 | 9/1992 |
| EP | 0 542 422 A1 | 5/1993 |
| EP | 0 574 267 A2 | 12/1993 |
| EP | 0 574 267 A3 | 12/1993 |
| EP | 0 622 457 A1 | 2/1994 |
| EP | 0 600 130 A2 | 6/1994 |
| EP | 0 687 501 B1 | 12/1995 |
| EP | 0 656 864 B1 | 3/1996 |
| EP | 0 727 665 A2 | 8/1996 |
| EP | 0 763 739 A1 | 3/1997 |
| EP | 0 819 941 A2 | 1/1998 |
| EP | 0 875 584 A2 | 4/1998 |
| EP | 0 843 176 A1 | 5/1998 |
| EP | 0 680 883 B1 | 12/1998 |
| EP | 0 889 328 A | 7/1999 |
| EP | 0 953 838 A1 | 11/1999 |
| EP | 0 640 828 B1 | 5/2000 |
| EP | 1 069 942 B1 | 1/2001 |
| EP | 1 075 328 B1 | 2/2001 |
| EP | 0 875 584 A3 | 5/2001 |
| EP | 0 752 971 B1 | 6/2001 |
| EP | 1 205 756 A2 | 5/2002 |
| EP | 1 248 170 B1 | 10/2002 |
| EP | 1 273 919 A1 | 1/2003 |
| EP | 0 687 502 B1 | 3/2003 |
| EP | 1 288 758 B1 | 3/2003 |
| EP | 1 326 077 B1 | 9/2004 |
| EP | 1 557 961 A1 | 7/2005 |
| EP | 1 712 971 A2 | 10/2006 |
| EP | 1 712 971 A3 | 10/2006 |
| EP | 1 398 729 B1 | 10/2007 |
| EP | 1 024 355 B1 | 3/2008 |
| EP | 0 885 958 B1 | 6/2008 |
| EP | 1 138 784 B1 | 10/2008 |
| EP | 1 623 764 B1 | 2/2009 |
| EP | 1 614 470 B1 | 3/2009 |
| EP | 1 721 671 B1 | 10/2009 |
| EP | 1 731 222 B1 | 3/2010 |
| EP | 2 295 144 A | 3/2011 |
| EP | 2 316 570 A2 | 5/2011 |
| EP | 2 316 571 A2 | 5/2011 |
| EP | 2 316 572 A2 | 5/2011 |
| EP | 2 148 205 B1 | 1/2013 |
| GB | 2 101 514 A | 1/1983 |
| GB | 2 203 243 A | 10/1988 |
| JP | 62-148858 A | 7/1987 |

(56) References Cited

FOREIGN PATENT DOCUMENTS

| | | |
|---|---|---|
| JP | 01-211500 A1 | 8/1989 |
| JP | 02-025754 A2 | 1/1990 |
| JP | 05-184397 A | 7/1993 |
| JP | 05-219933 A | 8/1993 |
| JP | 05-281239 A | 10/1993 |
| JP | 06-011512 A | 1/1994 |
| JP | 06-197797 A | 7/1994 |
| JP | 06-327476 A | 11/1994 |
| JP | 07-049346 A | 2/1995 |
| JP | 07-75544 A | 3/1995 |
| JP | 07-191042 A | 7/1995 |
| JP | 07-213586 A | 8/1995 |
| JP | 07-107999 B2 | 11/1995 |
| JP | 07-301637 A | 11/1995 |
| JP | 07-333230 A | 12/1995 |
| JP | 08-9957 A | 1/1996 |
| JP | 08-62224 A | 3/1996 |
| JP | 08-211071 A | 8/1996 |
| JP | 08-285857 A | 11/1996 |
| JP | 08-286749 A | 11/1996 |
| JP | 08-320274 A | 12/1996 |
| JP | 09-021805 A | 1/1997 |
| JP | 09-080056 A | 3/1997 |
| JP | 09-089902 A | 4/1997 |
| JP | 09-89907 A | 4/1997 |
| JP | 09-121899 A | 5/1997 |
| JP | 09-329602 A | 12/1997 |
| JP | 10-062426 A | 3/1998 |
| JP | 11-503315 A | 3/1999 |
| JP | 2000-500331 A | 1/2000 |
| JP | 3007571 B2 | 2/2000 |
| JP | 2001-503730 A | 3/2001 |
| JP | 2002-296286 A | 10/2002 |
| JP | 2006-317330 A | 11/2006 |
| JP | 2007-249632 A | 9/2007 |
| JP | 2008-032652 A2 | 2/2008 |
| JP | 4511034 A | 5/2010 |
| JP | 4662580 A | 3/2011 |
| WO | 88/01302 A1 | 2/1988 |
| WO | 88/10315 A1 | 12/1988 |
| WO | 89/02476 A1 | 3/1989 |
| WO | 90/06042 A2 | 6/1990 |
| WO | 90/08840 A1 | 8/1990 |
| WO | 91/15768 A1 | 10/1991 |
| WO | 91/16675 A1 | 10/1991 |
| WO | 93/07292 A1 | 4/1993 |
| WO | 93/25912 A2 | 12/1993 |
| WO | 93/25912 A3 | 12/1993 |
| WO | 93/25913 A1 | 12/1993 |
| WO | 95/08774 A2 | 3/1995 |
| WO | 95/11454 A1 | 4/1995 |
| WO | 95/21382 A2 | 8/1995 |
| WO | 95/30139 A1 | 11/1995 |
| WO | 95/35390 A1 | 12/1995 |
| WO | 96/29602 A1 | 9/1996 |
| WO | 96/31781 A1 | 10/1996 |
| WO | 96/40990 A1 | 12/1996 |
| WO | 97/03348 A1 | 1/1997 |
| WO | 97/05492 A1 | 2/1997 |
| WO | 97/16561 A1 | 5/1997 |
| WO | 97/22882 A1 | 6/1997 |
| WO | 97/31105 A1 | 8/1997 |
| WO | 97/34908 A1 | 9/1997 |
| WO | 97/46707 A2 | 12/1997 |
| WO | 98/18008 A1 | 4/1998 |
| WO | 99/25476 A2 | 5/1999 |
| WO | 99/28724 A1 | 6/1999 |
| WO | 99/57561 A2 | 11/1999 |
| WO | 00/08472 A2 | 2/2000 |
| WO | 00/08472 A3 | 2/2000 |
| WO | 00/15481 A1 | 3/2000 |
| WO | 00/38046 A1 | 6/2000 |
| WO | 00/67547 A2 | 11/2000 |
| WO | 01/44510 A2 | 6/2001 |
| WO | 03/046412 A1 | 6/2003 |
| WO | 03/097808 A2 | 11/2003 |
| WO | 2004/013640 A1 | 2/2004 |
| WO | 2006/021052 A1 | 3/2006 |
| WO | 2006/068470 A1 | 6/2006 |
| WO | 2007/094744 A1 | 8/2007 |
| WO | 2008/030914 A2 | 3/2008 |
| WO | 2008/043393 A1 | 4/2008 |
| WO | 2008/057375 A2 | 5/2008 |
| WO | 2008/067847 A1 | 6/2008 |
| WO | 2009/068555 A1 | 6/2009 |
| WO | 2009/097263 A1 | 8/2009 |
| WO | 2009/150632 A2 | 12/2009 |
| WO | 2009/150632 A3 | 12/2009 |
| WO | 2010/017528 A2 | 2/2010 |
| WO | 2010/080340 A1 | 7/2010 |
| WO | 2010/081606 A1 | 7/2010 |
| WO | 2011/013701 A1 | 2/2011 |
| WO | 2011/028166 A1 | 3/2011 |
| WO | WO 2011091013 A1 * | 7/2011 ............ B01L 3/5453 |
| WO | 2012/090795 A1 | 7/2012 |
| WO | 2012/158541 A1 | 11/2012 |

OTHER PUBLICATIONS

Abe et al., "Quantitation of Hepatitis B Virus Genomic DNA by Real-Time Detection PCR," J. Clin. Microbiol., 1999, 37(9):2899-2903, American Society for Microbiology, Washington D.C., USA.

ABI Prism® 373 DNA Sequencer With XL Upgrade—User's Manual, Mar. 2001, TOC-iii—Toc-v & 6-11-6-16, Applied Biosystems, USA.

ABI Product Catalogue, 1993-1994, "DNA Sequencing Reagents," p. 146, Applied Biosystems, USA.

Abravaya, "Strategies to Avoid Amplicon Contamination," in Nucleic Acid Amplification Technologies: Application to Disease Diagnosis, 1997, pp. 125-133, Eaton Pub. Co., Natick, USA.

Akane, "Identification of the heme compound copurified with deoxyribonucleic acid (DNA) from bloodstains, a major inhibitor of polymerase chain reaction (PCR) amplification", J. Forensic Sci., 1994, 39:362-72, Blackwell Pub., USA.

Akduman et al., "Evaluation of a Strand Displacement Amplification Assay (BD ProbeTec-SDA) for Detection of Neisseria gonorrhoeae in Urine Specimens," J. Clin. Microbiol., 2002, 40(1):281-282, American Society for Microbiology, Washington D.C., USA.

Amplification Technical Bulletin, "Comparison of TMA with PCR and LCR Amplification Methods," undated, Gen-Probe Incorporated, San Diego, USA, 1 page.

Analog Device; "±5 g to ±5 g, Low Noise, Low Power, Single/Dual Axis / MEMS® Accelerometers,"; http://hibp.ecse.rpi.edu/~connor.education/EISpecs/ADXL150_250_0.pdf;; Jan. 1, 1998; pp. 1-15.

Anderson et al., "Microfluidic Biochemical Analysis System," Transducers, International Conference on Solib-Slate Sensors and Actuators, Jun. 16-19, 1997, p. 477-480, IEEE Electron Devices Society, Piscataway, USA.

Anonymous, "GeneAmp optical reaction plate," Nature, 1998, 391(8):210, Nature Publishing Group, USA.

Armstrong et al., 1996, "Automated high throughput RT-PCR," Laboratory Robotics and Automation 8:311-315, VCH Publishers, USA.

Asper et al., "Laboratory Mechanization and Automation," in Laboratory Organization Automation, 1991, pp. 271-275, Walter, deGruyter, USA.

Astle, "Standards in Robotics and Instrucmentation," Society Updates, Working Group Updates, and Conference Highlights, J. Biomol. Screen., 1996, 1(4):161-172, Sage Publications, USA.

Bailey et al., "Robotic Nucleic Acid Isolation Using a Magnetic Bead Resin and an Automated Liquid Handler for Biological Agent Simulants,", JALA, Dec. 2003, 8:113-120.

Bassam. "Nucleic Acid Sequence Detection Systems: Revolutionary Automation for Monitoring and Reporting PCR Products" Australasian Biotechnology, 1996, 6:285-294, Australian Biotechnology Association, Australia.

Belgrader et al., "Automated DNA Purification and Amplification from Blood-Stained Cards Using a Robotic Workstation," Short Technical Reports, Biotechniques, 1995, 19(9):426-432, Informa Healthcare USA, Inc., UK.

(56) References Cited

OTHER PUBLICATIONS

Belgrader et al., "Automated Polymerase Chain Reaction Product Sample Preparation for Capillary Electrophoresis Analysis," J. Chromatogr. B Biomed. Appl., 1996, 683:109-114, Elsevier Science, Amsterdam, Netherlands.

Belgrader et al., "Automated Sample Processing Using Robotics for Genetic Typing of Short Tandem Repeat Polymorphisms by Capillary Electrophoresis," Laboratory Robotics and Automation, 1997, 9:3-7, Wiley & Sons Inc., USA.

Bieche et al., "Novel Approach to Quantitative Polymerase Chain Reaction Using Real-Time Detection: Application to the Detection of Gene Amplification in Breast Cancer," Int. J. Cancer, 1998, 78:661-666, Wiley-Liss, Inc., USA.

Billyard, et al., "Early detection of HIV-1 RNA from sero-conversion panels using Gen-Probe's transcription-mediated amplification," The San Diego Conference Nucleic Acid Technology: The Cutting Edge of Discovery, Nov. 6-8, 1997, Clin. Chem., 1997, 43(11):2221, Am. Assoc. for Clin. Chem., USA.

Borst et al., "False-Positive Results and Contamination in Nucleic Acid Amplification Assays: Suggestions for a Prevent and Destroy Strategy," Eur. J. Clin. Microbiol. Infect Dis., 2004, 23:289-299, Springer-Verlag, Berlin, Germany.

Boyd et al., "Robotics and the changing face of the clinical laboratory," Clin. Chem., 1996, 42(12):1901-1910, Washington DC American Association for Clinical Chemistry, USA.

Brochure, "Amplified Mycobacteria Direct Tests," undated, Gen-Probe Incorporated, San Diego, USA, 6 pages.

Brochure, "Introducing the AMPLIFIED *Mycobacterium tuberculosis* Direct (MTD) Test from Gen-Probe," Oct. 1996, Gen-Probe Incorporated, San Diego, USA, 2 pages.

Brochure, "The Future of Amplification Technology has Arrived," Oct. 1995, Gen-Probe Incorporated, San Diego, USA, 4 pages.

Buhlmann et al., "An Open Software Environment to Optimize the Productivity of Robotized Laboratories," J. Chromatogra. Sci., 1994, 32:243-248, Preston Technical Abstracts, Niles, USA.

Burg et al., "Real-time fluorescence detection of RNA amplified by Q beta replicase," Anal. Biochem., 1995, 230(2):263-272, Academic Press, Orlando, Florida, USA.

Bush et al., "Detection of human immunodeficiency virus type 1 RNA in plasma samples from high-risk pediatric patients by using the self-sustained sequence replication reaction," J. Clin. Microbiol., 1992, 30(2):281-286, American Society for Microbiology, Washington D.C., USA.

Butler et al., "Forensic DNA typing by capillary electrophoresis using the ABI Prism 310 and 3100 genetic analyzers for STR analysis," Electrophoresis, 2004, 25:1397-1412, Wiley-VCH Verlag GmbH & Co. KGaA, Germany.

Caprari, G. et al.; "The autonomous Micro Robot "Alice": a platform for scientific and commercial applications"; *Proceedings of the 1998 International Symposium on Micromechatronics and Human Science*, Nagoya, Japan; Nov. 25-28, 1998; pp. 1-5.

Carlson et al., "Laboratory Detection of Chlamydia trachomatis, Neisseria gonorrhoeae, and Other Sexually-Transmitted Agents," 97th General Meeting of the American Society for Microbiology, C-308, May 4-8, 1997, Miami Beach, USA.

Carrino et al., "Nucleic Acid Amplification Methods," J. Micorbiol. Methods, 1995, 23:3-20.

Check, "Real-time PCR for the rest of us," CAP Today, Jun. 2006, College of American Pathologists, Skokie, IL, USA, 6 pages.

Chemistry Guide, "ABI PRISM DNA Sequencing," 1995, pp. 1-3-1-6, The Perkin-Elmer Corporation, USA.

Chemistry Guide, "Automated DNA Sequencing," PE Applied Biosystems, 1998, pp. I-4-I-6, The Perkin-Elmer Corporation.

Cimino et al., "Post-PCR sterilization: a method to control carry-over contamination for the polymerase chain reaction," Nucleic Acids Res., 1991, 19(1):99-107, Oxford University Press, Oxford, United Kingdom.

Civitello et al., "A simple protocol for the automation of DNA cycle sequencing reactions and polymerase chain reactions," DNA Sequence—J. DNA Sequencing and Mapping, 1992, 3:17-23, Harwood Academic Publishers GmbH, UK.

Clewley, "Automation of the Polymerase Chain Reaction Part 2. Extraction—the Foundation for Success," Communicable Disease and Public Health, Jun. 1999, 2(2):147-148, Public Health Laboratory Service in association with the Scottish Centre for Infection and Environmental Health, London, United Kingdom.

Corkan et al., "Experiment Manager Software for an Automated Chemistry Workstation, Including a Scheduler for Parallel Experimentation," Chemometrics and Intelligent Laboratory Systems: Laboratory Information Management, 1992, 17:47-74, Elsevier Science Publishers, Amsterdam, Netherlands.

Corrected Request for Inter Partes Reexamination of U.S. Pat. No. 7,482,143, filed on Sep. 14, 2012, 121 pages.

Crotchfelt et al., "Detection of Chlamydia trachomatis by the Gen-Probe Amplified Chlamydia Trachomatis Assay (AMP CT) in Urine Specimens from Men and Women and Endocervical Specimens from Women," J. Clin. Microbiol., Feb. 1998, 36(2):391-394, American Society for Microbiology, Washington D.C., USA.

Dangler, ed., Nucleic Acid Analysis: Principles and BioApplications, 1996, pp. 1-3, 19, 68-75, 106-109, 116, 117, 144, 145, 157, 162 & 163, Wiley-Liss, Inc., USA.

Davis et al., "Amplification of DNA Using the Polymerase Chain Reaction," in Basic Methods in Molecular Biology, 2nd ed., 1994, p. 121, Appleton & Lange, Norwalk, USA.

Diamandis, "Automation of molecular diagnostics," Clinical Chemistry, 1996, 42:7-8, American Association for Clinical Chemistry, USA.

DiDomenico et al., "COBAS AMPLICOR™: fully automated RNA and DNA amplification and detection system for routine diagnostic PCR," Clin. Chem., 1996, 42(12):1915-1923, Washington DC American Association for Clinical Chemistry, USA.

Dieffenbach et al., "Setting Up a PCR Laboratory," Genome Rsearch, PCR Methods and Applications, 1993, 3:s2-s7, Cold Spring Harbor Laboratory, Cold Spring Harbor, USA.

Dragon, "Handling Reagents in the PCR Laboratory," Genome Research, PCR Methods and Applications, 1993, 3:s8-s9, Cold Spring Harbor Laboratory, Cold Spring Harbor, USA.

Dynal®, Technical Handbook. Molecular Biology, First Edition. "Dynabeads® biomagnetic separation system," 1992, 4 pages, Dynal AS, Norway.

Educational Guide, "New Directions in Molecular Diagnostic Testing," pp. 1-12, Rev. A, 2000, Gen-Probe Incorporated, San Diego, USA.

Erlich, "PCR Technology," in Encyclopedia of Molecular Biology and Molecular Medicine: Mass Spectrometry High Speed DNA Fragment Sizing to Plasma Lipoproteins, vol. 4, 1996, p. 337, VCH Verlagsgesellschaft mbH, Weinheim, Germany.

Espy et al., "Dependence of polymerase chain reaction product inactivation protocols on amplicon length and sequence composition," J. Clin. Microbiol., 1993, 31(9):2361-2365, American Society for Microbiology, Washington D.C., USA.

Farrell, Jr., "RT PCR" in RNA Method: A Laboratory Guide for Isolation and Characterization, 1998, 2nd ed., Chapter 15, pp. 296-307, Academic Press, San Diego, California, USA.

Feinberg, "A Technique for Radiolabeling DNA Restriction Endonuclease Fragments to High Specific Activity", Analytical Biochemistry, 1983, 132:6-13, Academic Press, USA.

Felder, "Automation of Preanalytical Processing and Mobile Robotics," in Handbook of Clinical Automation, Robotics, and Optimization, 1996, pp. 252-256, John Wiley & Sons, Inc., USA.

Findlay et al., "Automated Closed-Vessel System for in Vitro Diagnostics Based on Polymerase Chain Reaction," Clin. Chem., 1993, 39(9):1927-1933, American Association for Clinical Chemistry, Washington, D.C., USA.

Fiore et al., "The Abbott IMx automated benchtop immunochemistry analyzer system," Clin. Chem., 1988, 34 (9):1726-32, American Association for Clinical Chemistry, Washington D.C., USA.

Flexlink®; "TX45E puck handling (mx. 250g),"; located at http://www.flexlink.com/en/offering/conveyor-systems/pallet-and-puck-handling/x45e.jsp; last visited on Jul. 20, 2013; 2 pages.

(56) References Cited

OTHER PUBLICATIONS

Friendenberg et al., "Developing a fully automated instrument for molecular diagnostic assays," IVD Technology, 2005, 11(6), 6 pages, A Canon Communications, Los Angeles, USA.
Furrows et al., "'Good laboratory practice' in diagnostic laboratories using nucleic acid amplification methods," Clin. Microbiol. Infect., 2001, 7(5):227-229, Blackwell Science, Oxford, United Kingdom.
Gelmini et al., "Quantitative polymerase chain reaction-based homogeneous assay with fluorogenic probes to measure c-erbB-2 oncogene amplification," Clin. Chem., 1997, 43(5):752-758, American Association for Clinical Chemistry, Washington D.C., USA.
Genprobe; "Test Procedure Guide. AMPLIFIED *Mycobacterium tuberculosis* Direct (MTD) Test,"; 2000, 1 page.
Gerber et al., "Differential Transcriptional Regulation of the Two Vascular Endothelial Growth Factor Receptor Genes," J. Biol. Chem., 1997, 272(38):23659-23667, The American Society for Biochemistry and Molecular Biology, Baltimore, USA.
Gibson et al., "A homogenous method for genotyping with fluorescence polarization," Clin. Chem., 1997, 43(8):1336-1341, American Association for Clinical Chemistry, Washington D.C., USA.
Gibson et al., "A novel method for real time quantitative RT-PCR," Genome Methods, 1996, 6:995-1001, Cold Spring Harbor Laboratory Press, Cold Spring Harbor, USA.
Giesendorf et al., "Molecular beacons: a new approach for semiautomated mutation analysis," Clin. Chem., 1998, 44(3):482-486, American Association for Clinical Chemistry, Washington D.C., USA.
Gilgen et al., "Hydroxyquinoline overcomes PCR inhibition by UV-damaged mineral oil," Nucleic Acids Res., 1995, 23(19):4001-4002, Oxford University Press, Oxford, United Kingdom.
Ginocchio, "Life Beyond PCR: Alternative Target Amplification Technologies for the Diagnosis of Infectious Diseases, Part II," Clinical Microbiology Newsletter, 2004, 26(17):129-136, Elsevier Science, New York, USA.
Godfrey-Faussett, "Molecular Diagnosis of Tuberculosis: The Need for New Diagnostic Tools," Thorax, 1995, 50(7):709-711, British Medical Association, London, United Kingdom.
Greenstein, "Preparing and Using M13-Derived Vectors," Current Protocols in Molecular Biology, published 1990, §1.151 and 1.15.4, J. Wiley and Sons, USA.
Haas, "Clinical Instrumentation (General Chemistry and Immunoassay Analyzers)," Anal. Chem., 1993, 65(12):444R-449R, American Chemical Society, Washington D.C., USA.
Haglund et al., "Polymerase Chain Reaction," in Forensic Taphonomy: the Postmortem Fate of Human Remains, 1997, p. 114-115, CRC Press LLC, Boca Raton, USA.
Hartley et al., "Dealing with Contamination: Enzymatic Control of Carryover Contamination in PCR," Genome Research, PCR Methods and Applications, 1993, 3:s10-s14, Cold Spring Harbor Laboratory, Cold Spring Harbor, USA.
Hawker, "Laboratory Automation: Total and Subtotal," Clin. Lab. Med., 2007, 27:749-770, Elsevier Health Sciences Division, Philadelphia, USA.
Hawkes et al., "Asymptomatic carriage of *Haemophilus ducreyi* confirmed by the polymerase chain reaction," J. Genitourin. Med., 1995, 71:224-227.
Hawkins et al., "A Magnetic Attraction to High-Throughput Genomics," Science, 1997, 276:1887 & 1889 (p. 1888 omitted—advertisement only), Washington, DC: American Association for the Advancement of Science, USA.
Hawkins et al., "Thermal Cycle DNA Sequence Setup Using a Modified Lab Workstation," LRA, 1995, 7:117-122, VCH Publishers, New York City, USA.
Hedrum et al., "Immunomagnetic Recovery of *Chlamydia trachomatis* from Urine with Subsequent Colorimetric DNA Detection," PCR Methods Appl., 1992, 2:167-171, Cold Spring Harbor Laboratory Press, Cold Spring Harbor, USA.

Heid et al., "Real Time Quantitative PCR," Genome Research, 1996, 6:986-994, Cold Spring Harbor Laboratory Press, Cold Spring Harbor, USA.
Hellyer et al., "Letter to the Editor: Specificity of IS6110-Based Amplification Assays for *Mycobacterium tuberculosis* Complex," J. Clin. Microbiol., 1997, 35(3):799-801, American Society for Microbiology, Washington D.C., USA.
Herring et al., "ELISA Automation: A Biomek 1000 to Biomek 2000 Comparison of Clinical ELISAs", Application Information, 1995, Beckman Industries, Inc., USA.
Herrmann et al., "General Aspects of Sample Preparation," in Ancient DNA: Recovery and Analysis of Genetic Material from Paleontological, Archaeological, Museum, Medical, and Forensic Specimens, 1994, pp. 63-64, Springer-Verlag, New York City, USA.
Hicks et al., "Beckman/Sagian "Core" Molecular Biology System,", T-1845A, Beckman Instruments, Inc., 1997, 4 pages.
Higuchi et al., "Kinetic PCR Analysis: Real-time Monitoring of DNA Amplification Reactions," Bio/Technology, 1993, 11(9):1026-30, Nature Publishing Group, New York, USA.
Higuchi et al., "Simultaneous Amplification and Detection of Specific DNA Sequences," Bio/Technology, 1992, 10:413-417, Nature Publishing Company, New York, USA.
Hildebrandt et al., Development of an Automated Sample Preparation Method for HCV, J. Microbiol. Methods, 1997, 30:235-253, Abstract 17, 1 page, Elsevier Biomedical, Amsterdam, Netherlands.
Hill et al., "The Polymerase Chain Reaction in Molecular and Micro-biology," Biotechnol. Genet. Eng. Rev., 1992, 10:343-377, Taylor & Francis, UK.
Hill, "Gen-Probe Transcription-Mediated Amplification: System Principles," Jan. 1996, Gen-Probe Incorporated, San Diego, USA, 4 pages.
Hill, "How Full Automation of Molecular Diagnostic Testing Can Increase Accuracy, Lab Efficiency, Cost Savings," Issue Stories, Jul. 2004, 3 pages, Clinical Lab Products, Los Angeles, USA.
Hill, "Molecular diagnostic testing for infectious diseases using TMA technology," Expert Rev. Mol. Diagn., 2001, 1 (4):445-455, Future Drugs Ltd., London, United Kingdom.
Hill, "Molecular Diagnostic Tests for Sexually Transmitted Infections in Women," in Infectious Diseases in Obstetrics and Gynecology, 2008, 6th ed., pp. 612-623, Informa plc, St. Helier, Jersey.
Hill, "Molecular Diagnostics for Infectious Diseases," J. Clin. Ligand Assay, 1996, 19(1):43-52, Clinical Ligand Assay Society, Wayne, Michigan, USA.
Hoad et al., "Virus Genome Detection by the PCR," in Practical Molecular Virology: Viral Vectors for Gene Expression, 1991, pp. 75-76, Humana Press, Totowa, USA.
Holland et al., "Detection of specific polymerase chain reaction product by utilizing the 5'→3' exonuclease activity of Thermus aquaticus DNA polymerase," Biochemistry, 1991, 88:7276-7280, Proc. Natl. Acad. Sci. USA, Washington D.C., USA.
Holmberg et al., "Automatic Preparation of DNA Templates for Sequencing on the ABI Catalyst Robotic Workstation," Automated DNA Sequencing and Analysis, 1994, Academic Press Inc., San Diego, USA.
Hunkapiller, "Advances in DNA sequencing technology," Curr. Opin. Genet. Dev., 1991, 1:88-92, Elsevier, UK.
International Search Report and Written Opinion dated Dec. 7, 2012 for PCT Patent Application No. PCT/US2011/045107, 18 pages.
International Search Report and Written Opinion dated Aug. 9, 2012 for PCT Patent Application No. PCT/US2012/037585, 10 pages.
International Search Report and Written Opinion dated Feb. 15, 2013 for PCT Application No. PCT/US2012/063923, 12 pages.
International Search Report and Written Opinion dated Feb. 15, 2013 for PCT Application No. PCT/US2012/063914, 9 pages.
International Search Report and Written Opinion dated Jun. 12, 2013 for PCT Patent Application No. PCT/US2012/063888, 18 pages.
International Search Report and Written Opinion dated Mar. 19, 2013 for PCT Patent Application No. PCT/US2012/063929, 13 pages.
International Search Report and Written Opinion dated Nov. 6, 2013 for PCT Patent Application No. PCT/US2012/063918, 22 pages.
International Search Report and Written Opinion dated Oct. 4, 2013 for PCT Patent Application No. PCT/US2012/063931, 24 pages.

(56) References Cited

OTHER PUBLICATIONS

International Search Report and Written Opinion dated Sep. 30, 2013 for PCT Patent Application No. PCT/US2012/063930, 37 pages.

Invitation to Pay Additional Fees mailed on Mar. 1, 2013 for PCT Patent Application No. PCT/US2012/063918, 6 pages.

Invitation to Pay Additional Fees mailed on Mar. 19, 2013 for PCT Patent Application No. PCT/US2012/063930, 8 pages.

Invitation to Pay Additional Fees mailed on Mar. 25, 2013 for PCT Patent Application No. PCT/US2012/063931, 8 pages.

Invitation to Pay Additional Fees mailed on Mar. 6, 2013 for PCT Patent Application no. PCT/US2012/063888, 6 pages.

Invitrogen; Manual, "Dynabeads® DNA DIRECT™ Blood" Cat. No. 631.02 "For the isolation of PCR-ready genomic DNA from blood" Rev. o. 006, Invitrogen, *Dynal® Invitrogen Bead Separations*, 2007.

Jaklevic, "Automation of High-Throughput PCR Assays," Laboratory Robotics and Automation, 1996; 8(5):277-286, John Wiley & Sons Inc., USA.

Jakobsen et al., "Direct mRNA Isolation Using Magnetic Oligo (dT) Beads: A Protocol for All Types of Cell Cultures, Animal and Plant Tissues," in Advances in Biomagnetic Separation, 1994, pp. 61-71, Eaton Publishing, USA.

Jaton et al., "Development of polymerase chain reaction assays for detection of Listeria monocytogenes in clinical cerebrospinal fluid samples," J. Clin. Microbiol., 1992, 30(8):1931-1936, American Society for Microbiology, Washington D.C., USA.

Jungkind et al., "Evaluation of Automated COBAS AMPLICOR PCR System for Detection of Several Infectious Agents and Its Impact on Laboratory Management," J. Clin. Microbiol., 1996, 34(11):2778-2783, American Society for Microbiology, Washington, D.C., USA.

Kalinina et al., "Nanoliter scale PCR with TaqMan detection," Nucleic Acids Res., 1997, 25(10):1999-2004, Oxford University Press, Oxford, United Kingdom.

Kapperud et al., "Detection of Pathogenic Yersinia enterocolitica in Foods and Water by Immunomagnetic Separation, Nested Polymerase Chain Reactions, and Colorimetric Detection of Amplified DNA," Appl. Environ. Microbiol., 1993, 59(9):2938-2944, American Society for Microbiology, Washington, D.C., USA.

Kasper, "Automated Instrumentation (Generic)," in Clinical Laboratory Instrumentation and Automation: Principles, Applications, and Selection, 1994, pp. 184-205, W.B. Saunders Company, USA.

Kaufman et al., "Direct Sequencing by PCR," in Handbook of Molecular and Cellular Methods in Biology and Medicine, 1995, pp. 233-235, CRC Press, USA.

Kendrew et al., "Polymerase Chain Reaction," in the Encyclopedia of Molecular Biology, 1994, pp. 864-865, Blackwell Science Ltd., Cambridge, USA.

Khalil "Automation and Use of Robotics in Nucleic Acid Amplification Assays," in Nucleic Acid Amplification Technologies: Application to Disease Diagnosis, 1997, p. 151-164, Eaton Pub. Co., Natick, USA.

Kolk et al., "Development of Individual and Multiplex Assays for the Detection of HIV and HCV," 13th Annual Clinical Virology Symposium and Annual Meeting of the Pan American Society for Clinical Virology, M7, Apr. 27-30, 1997, Clearwater Beach, USA.

Kolmodin et al., "Basic Principles and Routine Practice," in PCR Cloning Protocols From Molecular Cloning to Genetic Engineering, 1997, pp. 3-5, Humana Press, Totowa, USA.

Kost, G. J., *Handbook of Clinical Automation, Robotics, and Optimization*; Chapters 1, 10, and 12-14; 1996 by John Wiley & Sons, Inc.; 189 pages total.

Kretz et al., "Cycle sequencing," PCR Methods and Applications, 1994, 3:S107-S112, Cold Spring Harbor Laboratory, Cold Spring Harbor Press, USA.

Krieg, "Quantification of RNA by Competitive RT PCR," in a Laboratory Guide to RNA, 1996, p. 210, Wiliey-Liss, New York City, USA.

Krieg, ed., "Quantitation of RNA Transcripts Using RT-PCR," in a Laboratory Guide to RNA: Isolation, Analysis, and Synthesis, 1996, pp. 176-190, John Wiley & Sons, Inc., USA.

Kwok et al., "Avoiding False Positive with PCR," Nature, 1989, 339:237-238, Nature Publishing Group, Basingstoke, USA.

Landry, "False-Positive Polymerase Chain Reaction Results in the Diagnosis of Herpes Simplex Encephalitis," J. Infect. Dis., 1995, 172(6):1641-1642, University of Chicago Press, Chicago, USA.

Lay et al., "Real-time fluorescence genotyping of factor V Leiden during rapid-cycle PCR," Clin. Chem., 1997, 43(12):2262-2267, American Association for Clinical Chemistry, Washington D.C., USA.

Lee et al., "Direct Identification of *Vibrio vulmificus* in Clinical Specimens by Nested PCR," J. Clin. Microbial., 1998, 36 (10):2887-2892, American Society for Microbiology, Washington D.C., USA.

Lee et al., "Nucleic Acid Amplification Technologies: Application to Disease Diagnosis," BioTechniques Books, 1997, pp. 1-286, Eaton Publishing, Massachusetts, USA.

Leone et al., "Molecular beacon probes combined with amplification by NASBA enable homogeneous, real-time detection of RNA," Nucleic Acids Res., 1998, 26(9): 2150-2155, Oxford University Press, Oxford, United Kingdom.

Lisby, "Application of Nucleic Acid Amplification in Clinical Microbiology," in Methods in Molecular Biology: PCR in Bioanalysis, 1998, pp. 1-29, Humana Press, Totowa, USA.

Little et al., "Recent Advances in Robotic Automation of Microplate Assays," Lab. Info. Mgmt., 1994, 26:89-99, Elsevier Science, Amsterdam, Netherlands.

Livak et al., "Oligonucleotides with Fluorescent Dyes at Opposite Ends Provide a Quenched Probe System Useful for Detecting PCR Product and Nucleic Acid Hybridization," PCR Methods and Applications, 1995, 4:357-362, Cold Spring Harbor Laboratory Press, Cold Spring Harbor, New York, USA.

Lo et al., "Quantitative Analysis of Fetal DNA in Maternal Plasma ad Serum: Implications for Noninvasive Prenatal Diagnosis," 1998, Am. J. Hum. Genet., 62:768-775, American Society of Human Genetics, Baltimore, USA.

Lo, "Setting Up a PCR Laboratory," in Methods in Molecular Medicine: Clinical Applications of PCR, 1998, pp. 12-17, Humana Press, Totowa, USA.

Longo, "Use of uracil DNA glycosylase to control carry-over contamination in polymerase chain reactions" Gene, 1990, 93: 125-128, Elsevier/North-Holland, Amsterdam.

Lundeberg et al., "Solid-Phase Technology: Magnetic Beads to Improve Nucleic Acid Detection and Analysis," Biotechnol. Annu. Rev., 1995, 1:373-401, Elsevier Science, Amsterdam, Netherlands.

Mabilat et al., "Routine Identification of *Mycobacterium tuberculosis* Complex Isolates by Automated Hybridization," J. Clin. Microbiol., 1994, 32(11):2702-2705, American Society for Microbiology, Washington, D.C., USA.

Magnemotion; "MagneMover™ LITE,"; located at http://www.magnemotion.com/industrial-automation/magmoverlite.cfm; last visited on Jul. 20, 2013; 3 pages.

Mahan et al., "An Automated System for Infectious Disease Diagnosis with Q-Beta Replicase Amplification," in New Horizons in Gene Amplification Technologies: Proceedings of a CHI Meeting, 1994, Cambridge, USA, 25 pages.

Mangiapan, "Sequence capture-PCR improves detection of mycobacterial DNA in clinical specimens" J Clin Microbiol., 1996, 34: 1209-1215, American Society for Microbiology, USA.

Martin et al., "PCR and Its Modifications for the Detection of Infectious Disease," Nucleic Acid Amplification Technologies: Application to Disease Diagnosis, 1997, p. 79-100, Eaton Pub. Co., Massachusetts, USA.

McCreedy et al., "Laboratory Design and Work Flow," Diagnostic Molecular Microbiology Principles and Applications, 1993, p. 149-159, Mayo Foundation, Rochester, USA.

McDonough et al., High Throughput Assay for the Simultaneous or Separate Detection of Human Immunodeficiency Virus (HIV) and Hepatitis Type C Virus (HCV), Infusionsther. Transfusionsmed, 1998, 25:164-169, Karger GmbH, Germany.

(56) References Cited

OTHER PUBLICATIONS

Meng et al., "TURBO PCR—An Integrated Robotic System for Continuously Setting Up and Running Multiple PCR Reactions," DOE Human Genome Program Contractor-Grantee Workshop IV, Nov. 13-17, 1994, Santa Fe, New Mexico, 1 page.
Mercier et al., "Direct PCR from whole blood, without DNA extraction," Nucleic Acids Res., 1990, 18(19):5908, Oxford University Press, Oxford, United Kingdom.
Merel et al., "Completely Automated Extraction of DNA from Whole Blood," Clin. Chem., 1996, 42(8):1285-1286, American Association for Clinical Chemistry, USA.
Merel et al., "Perspectives on Molecular Diagnostics Automation," JALA, 2005, 10:342-350, Association for Laboratory Automation, Charlottesville, USA.
Mertes et al., Automatische genetische Analytik, 1997, forward and pp. 68, 69, 73 & 74, Wiley-VCH, Germany; German Language Reference.
Meyers, "PCR Technology," Molecular Biology and Biotechnology: A Comprehensive Desk Reference, 1995, pp. 642-646, VCH Publishers Inc., New York City, USA.
Mischiati et al., "Use of an Automated Laboratory Workstation for Isloation of Genomic Dna Suitable for PCR and Allele-Specific Hybridization," BioTechniques, 1993, 15(1):146-151, Eaton Pub. Co., Natick, USA.
Mizutani et al., "Magnetic Separation in Molecular Studies of Human Leukemia," in Advances in Biomagnetic Separation, 1994, p. 127-133, Eaton Publishing, USA.
Mondada, Francesco et al.; "The e-Puck, a Robot Designed for Education in Engineering", *Proceedings of the 9th Conference on Autonomous Robot Systems and Competitions*, Castelo Branco, Portugal; May 7, 2009; vol. 1; Issue 1; pp. 59-65.
Muller et al., "Evaluation des klinish-chemischen Analysensystems Technicon DAX 72," Lab. Med., 1992, 16:210-218, Am. Soc. For Clinical Pathology, USA, with English Summary.
Mullis, "Eine Nachtfahrt and die Polymerase-Kettenreaktion," Spektrum der Wissenschaft, 1950, pp. 60-67, Germany.
Muramatsu et al., "Molecular Cell Biology Dictionary," 1997, Tokyo Kagaku Dojin Publisher, Tokyo, Japan, English Translation, 10 pages.
Nace, "Automation in Molecular Diagnostics: A Pleasant Surprise," Advance for Medical Laboratory Professionals, 2006, 14(11):64, Merion Publications, King of Prussia, PA, USA.
Nazarenko et al., "A closed tube format for amplification and detection of DNA based on energy transfer," Nucleic Acids Res., 1997, 25(12):2516-2521, Oxford University Press, Oxford, United Kingdom.
Neumaier et al., "Fundamentals of Quality Assessment of Molecular Amplification Methods in Clinical Diagnostics," Clin. Chem., 1998, 44(1):12-26, American Society for Clinical Chemistry, Washington D.C., USA.
Newton et al., "Instrumentation, Reagents and Consumables," PCR, 1996, 2nd ed., Chpt. 2, pp. 9-28, Bios Scientific, UK.
Nickerson et al., "Automated DNA Diagnostics Using an ELISA-based Oligonucleotide Ligation Assay," Proc. Natl. Acad. Sci. USA, 1990, 87:8923-8927, National Academy of Sciences, Washington, D.C., USA.
Niederhauser et al., "Direct Detection of *Listeria monocytogenes* Using Paramagnetic Bead DNA Extraction and Enzymatic DNA Amplificaiton,", Molecular and Cellular Probes, 1994, 8:223-228.
Noordhoek et al., "Reliability of Nucleic Acid Amplification for Detection of *Mycobacterium tuberculosis*: an International Collaborative Quality Control Study Among 30 Laboratories," J. Clin. Microbiol., 1996, 34(10):2522-2524, American Society for Microbiology, Washington D.C., USA.
Obata et al., "Development of a Novel Method for Operating Magnetic Particles, Magtration Technology, and Its Use for Automating Nucleic Acid Purification," J. Biosci. Bioeng., 2001, 91(5):500-503, Elsevier Science, Amsterdam, Netherlands.
Oehlenschlager et al., "Detection of HIV-1 RNA by nucleic acid sequence-based amplification combined with fluorescence correlation spectroscopy," Biochemistry, 1996, 93:12811-12816, Proc. Natl. Acad. Sci. USA, Washington D.C., USA.
Olive, "Q-Beta Replicase Assays for the Clinical Detection of Infectious Agents," in Nucleic Acid Amplification Technologies: Application to Disease Diagnosis, 1997, p. 110, Eaton Pub. Co., Natick, USA.
Olsvik et al., "Magnetic Separation in Laboratory Diagnosis of Infectious Diseases," in Advances in Biomagnetic Separation, 1994, pp. 149-158, Eaton Publishing, USA.
Olsvik et al., "Magnetic Separation Techniques in Diagnostic Microbiology," Clin. Microbiol. Rev., 1994, 7(1):43-54, American Society for Microbiology, Washington, D.C., USA.
Olympus Corporation, "Olympus News Release: Automated Chemistry Analyser AU1000," 1997, http://www.olympus-global.com/en/news/1997a/nr970421au1000e.jsp, downloaded Jun. 17, 2013, USA, 3 pages.
Oste, "Polymerase Chain Reaction," Product Application FOCUS, BioTechniques, 1988, 6(2):162-167, Informa Healthcare USA, Inc., UK.
Overbergh et al., "Quantification of Murine Cytokine mRNAs Using Real Time Quantitative Reverse Transcriptase PCR," Cytokine, 1999, 11(4):305-312, Academic Press, USA.
Package Insert, "APTIMA® Assay for *Neisseria gonorrhoeae*," IN0148-01-REG, Rev. 1, Nov. 2004, Gen-Probe Incorporated, San Diego, USA, 20 pages.
Package Insert, "APTIMA® HCV RNA Qualitative Assay," 500237 Rev. B, Jul. 2006, Gen-Probe Incorporated, San Diego, USA, 18 pages.
Package Insert, "GEN-PROBE® Amplified *Mycobacterium tuberculosis* Direct Test," IN0006 Rev. A, Feb. 24, 1994, Gen-Probe Incorporated, San Diego, USA, 14 pages.
Package Insert, "GEN-PROBE® AMPLIFIED™ Chlamydia Trachomatis Assay," IN0012 Rev. A, Jan. 6, 1997, Gen-Probe Incorporated, San Diego, USA, 17 pages.
Package Insert, "GEN-PROBE® AMPLIFIED™ Chlamydia Trachomatis Swab Specimen Preparation Kit," In0016 Rev. A, Jan. 6, 1997, Gen-Probe Incorporated, San Diego, USA, 3 pages.
Package Insert, "GEN-PROBE® AMPLIFIED™ Chlamydia Trachomatis Urine Specimen Preparation Kit," IN0017 Rev. A, Nov. 11, 1996, Gen-Probe Incorporated, San Diego, USA, 3 pages.
Package Insert, "GEN-PROBE® APTIMA® Combo 2 Assay," IN0037 Rev. A, Jun. 6, 2001, Gen-Probe Incorporated, San Diego, USA, 28 pages.
Package Insert, "GEN-PROBE® APTIMA Combo 2® Assay," 501011 Rev. A, Jan. 2007, Gen-Probe Incorporated, San Diego, USA, 44 pages.
Package Insert, "GEN-PROBE® APTIMA® Assay for *Chlamydia trachomatis*," IN0147-01, Rev. B, Apr. 2005, Gen-Probe Incorporated, San Diego, USA, 24 pages.
Package Insert, "Procleix® HIV-1/HCV Assay," IN0076-01-FDA, Rev. 3, Jun. 2004, Gen-Probe Incorporated, San Diego, USA, 28 pages.
Package Insert, "Procleix® HIV-1/HCV Assay," IN0076-02-FDA, Rev. 1, Jan. 2005, Gen-Probe Incorporated, San Diego, USA., 32 pages.
Package Insert, "Procleix® Ultrio™ Assay," IN0167EN, Rev. 1, Aug. 2004, Gen-Probe Incorporated, San Diego, USA, 44 pages.
Package Insert, "Procleix® WNV Assay," IN0155, Rev. 1, Apr. 2004, Gen-Probe Incorporated, San Diego, USA, 15 pages.
Paillard et al., "Direct nucleic acid diagnostic tests for bacterial infectious diseases: *Streptococcal pharyngitis*, pulmonary tuberculosis, vaginitis, chlamydial and gonococcal infections," MLO, Jan. 2004, pp. 10-15, Medical Laboratory Observer, NP Communications, LLC, Monroe Township, USA.
Panaccio et al., "PCR based diagnosis in the presence of 8% (v/v) blood," Nucleic Acids Res., 1991, 19(5):1151, Oxford University Press, Oxford, United Kingdom.
Patel et al., "Death from Inappropriate Therapy for Lyme Disease," Clin. Infect. Dis., 2000, 31:1107-1109, The University of Chicago Press, Chicago, USA.
Patterson et al., "Random and continuous-access immunoassays with chemiluminescent detection by Access automated analyzer,"

(56) References Cited

OTHER PUBLICATIONS

Clin. Chem., 1994, 40(11):2042-2045, American Association for Clinical Chemistry, Washington D.C., USA.

Pauwels et al., "Automated techniques in biotechnology," Current Opinion in Biotechnology, 1995, 6:111-117, Current Biology Ltd., London, United Kingdom.

Pawlotsky, "Measuring Hepatitis C Viremia in Clinical Samples: Can We Trust the Assays?" J. Hepatol., 1997, 26(1):1-4, Viral Hepatitis Foundation Bangladesh, Dhaka, Bangladesh.

Persing, "Diagnostic molecular microbiology. Current challenges and future directions," Diagn. Microbiol. Infect. Dis., 1993, 16(2):159-163, Elsevier Biomedical, New York, USA.

Petrik et al., "High throughput PCR detection of HCV based on semiautomated multisample RNA capture," J. Virol. Methods, 1997, 64:147-159, Elsevier/North-Holland Biomedical Press, Amsterdam, Netherlands.

Petrik et al., "Human Hepatic Glyceraldehyde-3-phosphate dehydrogenase Binds to the poly(U) tract of the 3' Non-Coding Region of Hepatitis C Virus Genomic RNA," J. General Virology, 1999, 80:3109-3113.

Piatek et al., "Molecular beacon sequence analysis for detecting drug resistance in *Mycobacterium tuberculosis*," Nature Biotechnology, 1998, 16:359-363, Nature America Publishing, New York, USA.

Request for Inter Partes Reexamination of U.S. Pat. No. 7,524,652, filed on Sep. 15, 2012, 134 pages.

Riggio et al., "Identification by PCR of Helicobacter pylori in subgingival plaque of adult periodontitis patients," J. Med. Microbiol., 1999, 48:317-322, The Pathological Society of Great Britain and Ireland.

Rosenblum et al., "New dye-labeled terminators for improved DNA sequencing patterns," Nucleic Acids Res., 1997, 25(22):4500-4504, Oxford University Press, UK.

Rudi et al., "Rapid, Universal Method to Isolate PCR-Ready DNA Using Magnetic Beads," Bio techniques, 1997, 22(3):506-511, Informa Healthcare USA, Inc., UK.

Rudi, et al., "Detection of Toxin-Producing Cyanobacteria by Use of Paramagnetic Beads for Cell Concentration and DNA Purification," 1998, Appl. Environ. Microbiol., 64(1):34-37, Am. Society of Microbiol., USA.

Schepetiuk et al., "Detection of *Chlamydia trachomatis* in Urine Samples by Nucleic Acid Tests: Comparison with Culture and Enzyme Immunoassay of Genital Swab Specimens," J. Clin Micorbiol., Dec. 1997, 35(12):3355-3357.

Shah et al., "Novel, Ultrasensitive, Q-Beta Replicase-Amplified Hybridization Assay for Detection of Chlamydia trachomatis," J. Clin. Microbiol., 1994, 32(11):2718-2724, American Society for Microbiology, USA.

Skeggs, "An automatic method for colorimetric analysis," Am. J. Clin. Pathol., 1957, 28:311-322, American Society of Clinical Pathologists, Chicago, USA.

Slatko, "Thermal Cycle Dideoxy DNA Sequencing," in Protocols for Gene Analysis (Methods in Molecular Biology), 1994, vol. 31, pp. 35-45, Humana Press Inc., USA.

Sloan et al., "Screening Yeast Artificial Chromosome Libraries with Robot-Aided Automation," GATA, 1993, 10(6):128-143, Elsevier Science Publishing Co., Inc., USA.

Smith et al., "Abbott AxSYM random and continuous access immunoassay system for improved workflow in the clinical laboratory," Clin. Chem., 1993, 39(10):2063-2069, American Association for Clinical Chemistry, Washington D. C., USA.

Smith et al., "Detection of *Mycobacterium tuberculosis* Directly from Sputum by Using a Prototype Automated Q-Beta Replicase Assay," J. Clin. Microbiol., 1997, 35(6):1477-1483, American Society for Microbiology, Washington, D.C., USA.

Smith et al., "Performance of an Automated Q-Beta Replicase Amplification Assay for *Mycobacterium tuberculosis* in a Clinical Trial," J. Clin. Microbiol., 1997, 35(6):1484-1491, Am. Society for Microbiology, USA.

Stanley et al., "A Survey of More Than 90 Commercially Available Luminometers and Imaging Devices for Low-Light Measurements of Chemiluminescence and Bioluminescence, Including Instruments for Manual, Automatic and Specialized Operation, for HPLC, LC, GLC and Microtitre Plates. Part 2: Photographs," J. Biolumin. Chemilumin., 1992, 7:157-169, John Wiley & Sons, Ltd., Chichester, Sussex, England.

Stanley, "Commercially Available Luminometers and Imaging Devices for Low-Light Level Measurements and Kits and Reagents Utilizing Bioluminescence or Chemiluminescence: Survey Update 3," J. Biolumin. Chemilumin., 1994, 9:123-125, John Wiley & Sons, Ltd., UK.

Stone et al., "Detection of rRNA from four respiratory pathogens using an automated Qβ replicase assay," Mol. Cell. Probes, 1996, 10:359-370, Academic Press Limited, San Diego, California, USA.

Suryanarayana et al., "Plasma SIV RNA Viral Load Determination by Real-Time Quantification of Product Generation in Reverse Transcriptase-Polymerase Chain Reaction," AIDS Res. Hum. Retroviruses, 1998, 14(2):183-189, Mary Ann Liebert, Inc., USA.

Sutton et al., "Hands Free Polymerase Chain Reaction," International Symposium on Laboratory Automation and Robotics, Oct. 17-20, 1993, p. 326-336, Boston, USA.

Sutton et al., "PCR Has Outgrown Appropriate Automated Instrumentation But Help is on the Way," Today's Chemist at Work, 1995, p. 42-48, American Chemical Society, Washington, D.C., USA.

Taos Inc. "TCS230 Programmable Color to Light-to-Frequency Converter," www.http?pdfl.alldatasheet.com/datasheet-pdf/view/96470/ETC/TCS230.html: Jan. 31, 2003, pp. 1-8.

Techne PHC-3 Thermal Cycler—Techni, Jun. 2009, Pegasus Scientific Inc., USA.

Tjian, "Purification and comparative properties of the delta and sigma subunits of RNA polymerase from Bacillus subtilis" Eur. J. Biochem., 1977, 74:149, Blackwell Science Ltd. On behalf of the Federation of European Biochemical Societies, UK.

Truchaud et al., "Liquid-Phase Reactions Started by Rehydrating Lyophilized Reagents in a Centrifugal Analyzer," Clin. Chem., 1985, 31(9):1506-1508, Am. Assoc. For Clin. Chem., USA.

Tyagi et al., "Extremely sensitive, background-free gene detection using binary proves and QB Replicase," Biochemistry, 1996, 93:5395-5400, Proc. Natl. Acad. Sci. USA, Washington D.C., USA.

Tyagi et al., "Molecular Beacons: Probes that Fluoresce upon Hybridization," Nature Biotechnology, 1996, 14:303-308, Nature Publishing Company, New York, USA.

Tyagi et al., "Multicolor molecular beacons for allele discrimination," Nat. Biotechnol., 1998, 16:49-53, Nature Publishing Group, USA.

Uckun et al., "Clinical Significance of MLL-AF4 Fusion Transcript Expression in the Absence of a Cytogenetically Detectable t(4;11)(q21;q23) Chromosomal Translocation," Blood, 1998, 92(3):810-821, American Society of Hematology, Washington D.C., USA.

Van Gemen, B. at al.; "The One-tube Quantitative HIV-1 RNA NASBA: Precision, Accuract and Application,"; 1995; *PCR Methods Appl.*; vol. 4; pp. 177-184.

Victor et al., "Laboratory Experience and Guidelines for Avoiding False Positive Polymerase Chain Reaction Results," Eur. J. Clin. Chem. Clin. Biochem., 1993, 31(8):531-535, Walter de Gruyter & Co., Berlin, Germany.

Vonderschmitt, ed., "Robots in the Clinical Laboratory," in Laboratory Automation Organization, 1991, pp. 576-577, Walter deGruyter, USA.

Voss et al., "Direct genomic fluorescent on-line sequencing and analysis using in vitro amplification of DNA," Nucl. Acids Res., 1989, 17(7):2517-2527, IRL Press, USA.

Walker et al., "Detection of *Mycobacterium tuberculosis* DNA with thermophilic strand displacement amplification and fluorescence polarization," Clin. Chem., 1996, 42(10):1604-1608, American Association for Clinical Chemistry, Washington D.C., USA.

Walker et al., "Strand displacement amplification (SDA) and transient-state fluorescence polarization detection of *Mycobacterium tuberculosis* DNA," Clin. Chem., 1996, 42(1):9-13, American Association for Clinical Chemistry, Washington D.C., USA.

(56) References Cited

OTHER PUBLICATIONS

Walter et al., "Fluorescence correlation analysis of probe diffusion simplifies quantitative pathogen detection by PCR," Proc. Natl. Acad. Sci. USA, 1996, 93:12805-12810, National Academy of Sciences, Washington D.C., USA.

Ward, ed., "Improving Laboratory Efficiency Through Workflow Analysis", in Clinical Laboratory Instrumentation and Automation: Principles, Applications, and Selection, 1994, pp. 453 & 457, W.B. Saunders Company, USA.

Webster's New World Dictionary, Third college Edition, 1988: Definition of Incubate, Incubator.

Whelan et al., "The Role of Nucleic Acid Amplification and Detection in the Clinical Microbiology Laboratory," Annu. Rev. Microbiol., 1996, 50:349-373, Annual Reviews, Palo Alto, USA.

Wilke et al., "Automation of Polymerase Chain Reaction Tests Reduction of Human Errors Leading to Contamination," Diagn. Microbiol. Infect. Dis., 1995, 21:181-185, Elsevier Sciences, New York City, USA.

Wilke et al., "Automation of Polymerase Chain Reaction Tests to Achieve Acceptable Contamination Rates," Clin. Chem., 1995, 41(4):622-623, American Association for Clinical Chemistry, Washington, D.C., USA.

Wittwer et al., "The LightCycler: a microvolume multisample fluorimeter with rapid temperature control," BioTechniques, 1997, 22:176-181, Informa Healthcare USA, Inc., London, United Kingdom.

Yohda et al., "Development of a Novel Laboratory Automation System for Molecular Biology," Kaguku-Koguku Symposium, 1998, p. 17-20.

Yourno et al., "A method for nested PCR with single closed reaction tubes," PCR Methods Appl., 1992, 2(1):60-65, Cold Spring Harbor Laboratory Press, Cold Spring Harbor, New York, USA.

Non-Final Office Action dated Sep. 5, 2014 for U.S. Appl. No. 13/671,454, 19 pages.

Notice of Allowance dated Jan. 30, 2015 for U.S. Appl. No. 13/671,454, 10 pages.

* cited by examiner

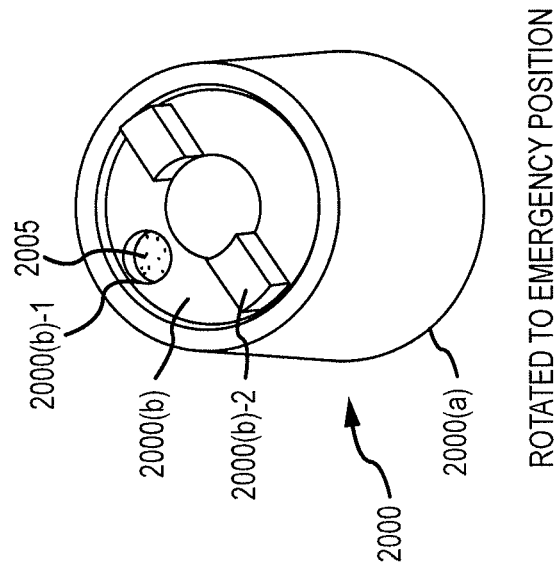
FIG. 8b ROTATED TO EMERGENCY POSITION
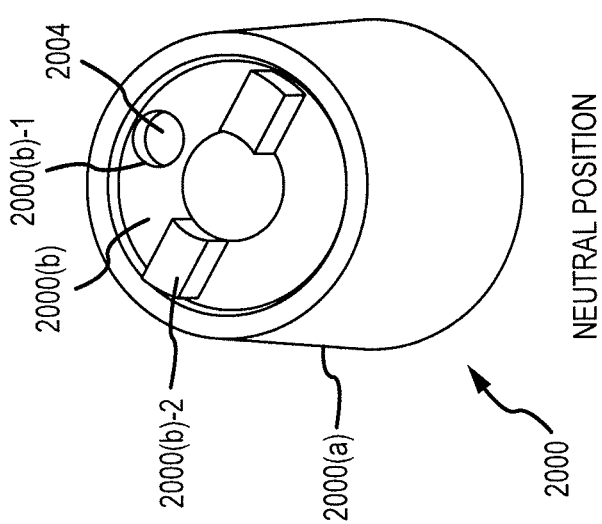
FIG. 8a NEUTRAL POSITION

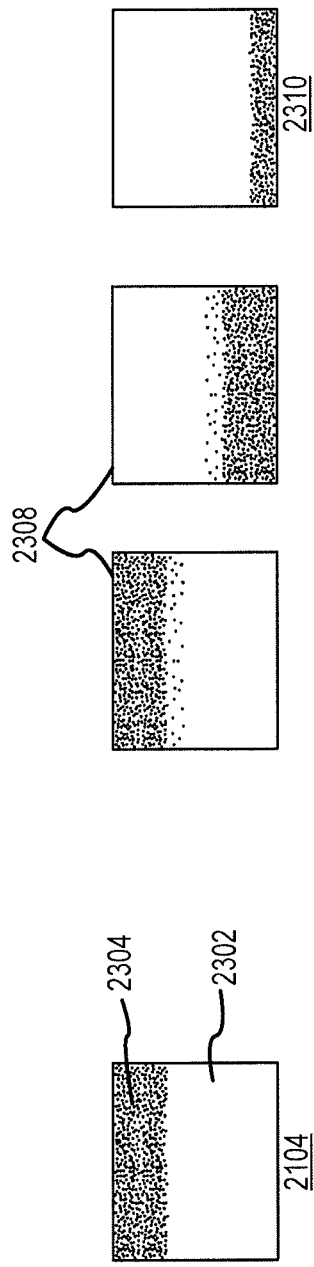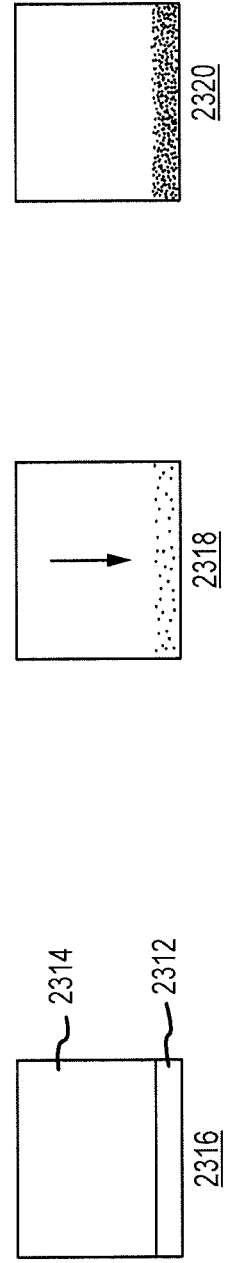

SAMPLE CONTAINER CAP WITH CENTRIFUGATION STATUS INDICATOR DEVICE

CROSS-REFERENCES TO RELATED APPLICATIONS

This application is a divisional of U.S. patent application Ser. No. 13/671,454, filed on Nov. 7, 2012, and entitled "Specimen Container Detection," which claims priority to U.S. Provisional Patent Application No. 61/556,667, filed Nov. 7, 2011 and entitled "Analytical System and Method for Processing Samples." U.S. patent application Ser. No. 13/671,454 also claims priority to U.S. Provisional Patent Application No. 61/616,994, filed Mar. 28, 2012 and entitled "Analytical System and Method for Processing Samples." U.S. patent application Ser. No. 13/671,454 also claims priority to U.S. Provisional Patent Application No. 61/680,066, filed Aug. 6, 2012 and entitled "Analytical System and Method for Processing Samples." All of these applications are herein incorporated by reference in their entirety for all purposes.

BACKGROUND

Conventional medical laboratory systems contain many segments for processing patient samples, some of which are automated and some of which require manual operation. Laboratory systems today have become more efficient due to those segments which have become automated. However, there are still several components of medical laboratory systems that can be automated in order to reduce the time it takes for an analysis of a sample, reduce the need for manual operation of the system, and reduce the space required by machinery.

Generally, the laboratory process can be organized into four phases: association, pre-analytical, analytical, and post-analytical. These four phases typically occur within any laboratory process. However, some conventional labs may have a process that uses standalone units throughout the lab while others may connect some of the units with a conveyance system to move the sample from unit to unit. These two styles have some common and some different processing needs. Additionally, some conventional labs may consistently process the same types of sample tubes (e.g., as in those from a kit) while others may have a wide range of tube types they must accommodate. Furthermore, many labs may have a preference for a particular manufacturer of an analyzer while others may use all of the analyzers from one manufacturer.

Thus, there is a need for a more efficient system and method for processing patient samples that can accommodate both a process using standalone units and units connected with a conveyance system, a variety of sample tube types, and analyzers from any manufacturer.

One aspect of automated laboratory systems relates to tube identification. Automatic tube identification is needed in a laboratory system so that the laboratory system knows how to process samples in the sample tubes.

Conventional tube-in-rack detection typically utilizes image analysis tools on 2-dimensional images acquired by one camera or a plurality of cameras in order to determine objects in the field of view of the cameras. This technology is well known in various fields, including, e.g., the analysis of pathology samples by microscopes.

In other fields, this technology may be used to identify objects in moveable loading or unloading means of a system, including, e.g., identifying drawers of a workbench. See, e.g., WO/2010/017528. A series of images can be taken by each camera during the opening and closing of the drawer and stitched together to generate an overview image. Within this overview image, single objects can be detected by image analysis.

In the field of laboratory automation systems, it is well known that single objects, such as a cap or closure of a sample tube, located in a holding rack can be identified by employing image analysis algorithms on top views of the hold racks. However, the image analysis algorithms are typically limited to the identification of only the single object and do not identify other details of the objects within the image.

Other tube identification mechanisms include the use of sample tube markers. Conventional sample tube markers used to identify a sample tube requiring immediate analysis typically include self-adhering labels (e.g., colored labels indicating urgency), "urgent" stickers, or simply a handwritten note indicating urgency on already existing labels. These urgent sample tube markers are inefficient and non-automated, requiring a laboratory technician to apply and/or handwrite the indication of urgency.

Additionally, conventional sample tube markers used to identify a centrifuged sample may include g-force sensitive labels. These labels measure whether there was an impermissibly high shock during transport. However, such labels are on the side of sample tubes, and as such cannot be easily reviewed or identified by overhead cameras and the like.

Embodiments of the invention address these and other problems, individually and collectively.

BRIEF SUMMARY

Embodiments of the technology relate to systems and methods for efficiently processing patient samples.

One embodiment of the invention is directed to a system. The system includes at least one image acquisition device configured to obtain one or more images of a sample container holder or a sample container in the sample container holder when positioned above the sample container holder or the sample container in the sample container holder. The system also comprises an image analysis device coupled to the at least one image acquisition device and configured to analyze, by a processor, the one or more images of the sample container holder or sample containers in the sample container holder, to determine (a) a presence, absence, or characteristic of the sample container holder, wherein the characteristic of the sample container holder comprises a color or shape of the sample container holder, or a label or marker associated with the sample container holder, or (b) a presence, absence or characteristic of the sample container in the sample container holder, wherein the sample container characteristic includes one or more of a color or shape of the sample container, or a label or marker associated with the sample container.

Another embodiment of the invention is directed to a method. The method comprises acquiring, by the at least one image acquisition device, at least one image of the sample container holder with the sample containers comprising samples, and analyzing, by an image analysis device, the at least one image. The at least one image is analyzed to determine (a) a presence, absence, or a characteristic of the sample container holder, wherein the characteristic of sample container holder comprises a color or shape of the sample container holder, or a label or marker associated with the sample container holder, or (b) a presence, absence or a characteristic of the sample container in the sample container holder, wherein the sample container characteristic includes one or more of a color or shape of the sample container holder, or a label or marker associated with the sample container.

Another embodiment of the invention is directed to a sample container cap comprising a cap body capable of covering a sample container body, and a movable element coupled to the cap body. The movable element is capable of indicating a status of the sample container for processing in a laboratory automation system.

Another embodiment of the invention is directed to a sample container cap comprising a sample cap body capable of covering an opening of the sample container. A centrifugation status indicator device is in the sample cap body.

These and other embodiments of the technology are described in further detail below.

BRIEF DESCRIPTION OF THE DRAWINGS

FIGS. 8(a)-8(b) depict one example of a top perspective view of a cap having an urgent sample indicator.

FIGS. 9(a)-9(b) depict exemplary color indicators of centrifugation indicators.

DETAILED DESCRIPTION

Figure 1:
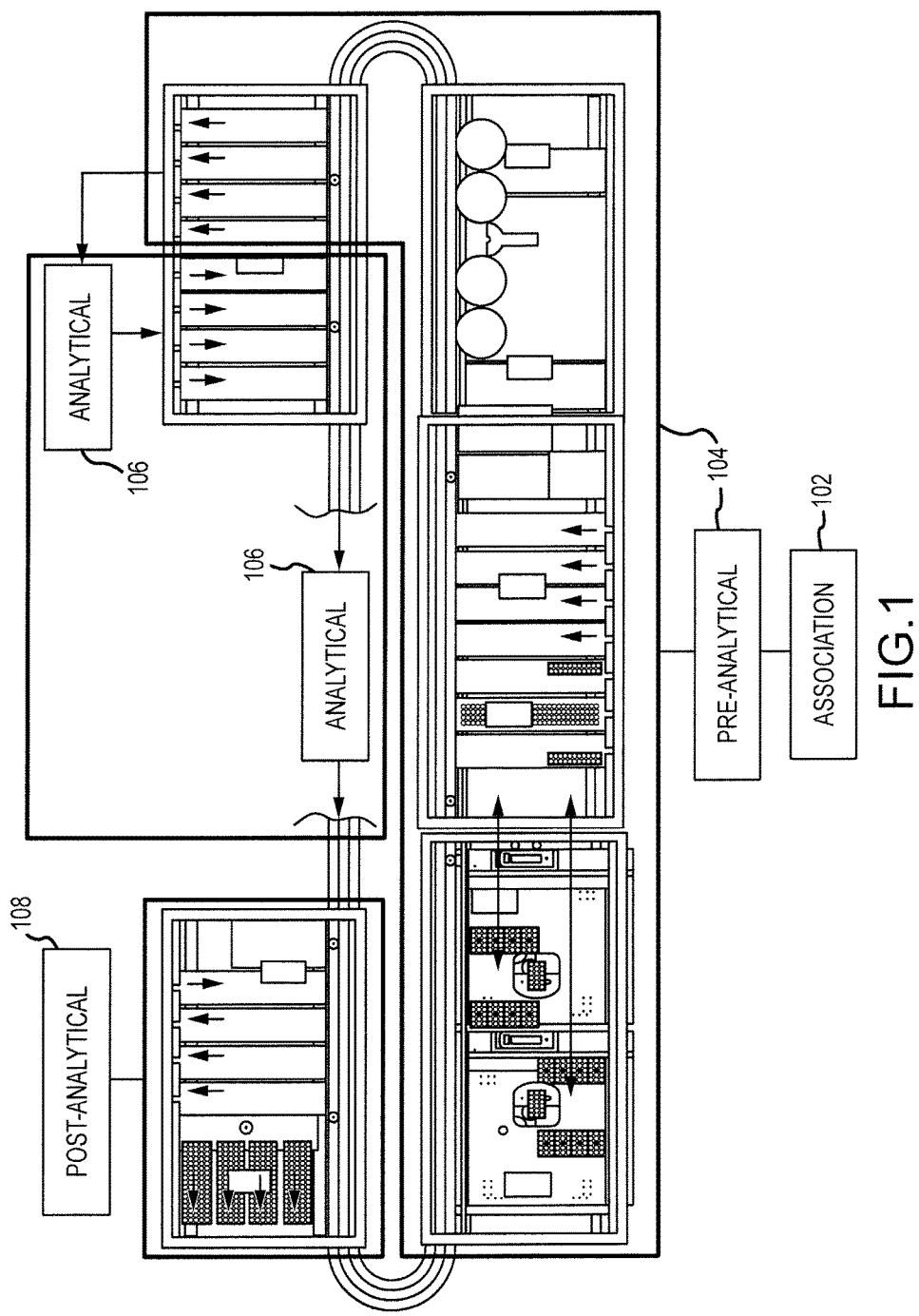
FIG. 1 shows a block diagram of components associated with phases of a laboratory automation system.

Embodiments of the invention relate to different ways to identify sample containers in an automated laboratory analysis system. One embodiment of the invention is directed to a system. The system includes at least one image acquisition device configured to obtain one or more images of a sample container holder or a sample container in the sample container holder when positioned above the sample container holder or the sample container in the sample container holder. The system also comprises an image analysis device coupled to the at least one image acquisition device and configured to analyze, by a processor, the one or more images of the sample container holder or sample containers in the sample container holder, to determine (a) a presence, absence, or characteristic of the sample container holder, wherein the characteristic of the sample container holder comprises a color or shape of the sample container holder, or a label or marker associated with the sample container holder, or (b) a presence, absence or characteristic of the sample container in the sample container holder, wherein the sample container characteristic includes one or more of a color or shape of the sample container, or labels and markers associated with the sample container.

In embodiments of the invention, a "sample container" may have any suitable shape or form. In some embodiments, the sample container may be in the form of a sample tube, which may have an aspect ratio of greater than about 3:1. Such sample containers may be made or any suitable material including plastic, glass, etc. They may further include a sample tube body with a closed end and an open end, as well as a cap that is structured to cover and attach to the open end of the sample tube body.

In embodiments of the invention, a "sample container holder" may be in any suitable shape or form, and may comprise any suitable material. In some cases, the sample tube holder may be in the form of a sample tube rack. Sample container holders may include an array of recesses that can receive sample containers (e.g., sample tubes). They may also comprise any suitable material including plastic.

As discussed above, many conventional laboratory systems may have a process that uses standalone units throughout the lab, requiring that the samples be manually transported between each standalone unit, while others may connect some of the units with a conveyance system to move the samples from unit to unit. Additionally, as discussed above, sample tube sizes and equipment from different manufacturers may be constraints in conventional laboratory systems. Such conventional technology is slow and inaccurate. Embodiments of the present technology can be used in a modular laboratory system which is capable of accommodating different laboratory units and transport systems, sample tube sizes, and manufacturers by using more universal components and by grouping functions required by most laboratory systems into five basic functional units: (1) manager, (2) centrifuge, (3), aliquotter, (4) output/sorter, and (5) storage units. These five basic functional units will be described in more detail below.

In embodiments of the invention, the laboratory system operates a controlled process using a central controller or scheduler. By keeping the samples under the control of an intelligent scheduler, the system provides efficient usage of every instrument. The system can maintain a consistent minimal turnaround time and maximizes the throughput of the entire system by maintaining control of the process and only delivering samples to instruments when those instruments are ready and available.

The laboratory system according to an embodiment of the invention further utilizes one or more robotic gripper units mounted on robotic arms. Each robotic arm unit has a robotic gripper for gripping sample tubes and may be equipped with one or more means for detecting information about sample tubes. The terms "gripper" and "robotic gripper" are used interchangeably herein.

Use of a plurality of robotic gripper units in the laboratory system also increases sample processing efficiency. For example, a first gripper, such as an input module gripper, identifies a sample tube and makes data measurements as described above. After the first gripper delivers the sample tube to a distribution area, a second gripper, such as a distribution area gripper, delivers a sample tube to a subsequent module such as a centrifuge module or conveyor. The use of multiple grippers allows an increase in processing efficiency over prior art systems that use only a single gripper to receive, identify, and load all samples on a conveyor track.

I. Overall System

A. Phases of Laboratory System

FIG. 1 depicts one embodiment of a medical laboratory system for processing patient samples. The laboratory system includes components associated with the association phase 102, the pre-analytical phase 104, the analytical phase 106, and the post-analytical phase 108.

1. Association Phase

The association phase 102 is the first phase in the laboratory process. During this phase, the patient information, the requested tests for the patient sample, and a unique laboratory identifier (e.g., a barcode) are associated with one another. While the association phase 102 could be automated, in some embodiments, the association phase is handled manually. For example, in some embodiments, a laboratory technician (hereinafter referred to as a "user") can assign a priority to the samples. The samples are loaded into racks or directly onto the system at specific entry points. Although grouping samples into a few basic priority levels (e.g., urgent or high priority, medium priority, low priority, etc.) may be desirable to provide a more consistent turn-around time, it is not necessary. Processing patient samples can be based on any priority defined by the user. However, if a priority is not specified, a priority can be assigned based on factors such as minimizing turnaround time, maximizing throughput, the availability of processes, etc.

2. Pre-Analytical Phase

The pre-analytical phase 104 includes preparing patient samples for analysis. During the pre-analytical phase 104, the patient and test information is deciphered, the process for analysis is planned, the quality checks are performed, the sample may be separated into its constituent components (e.g., centrifuged), the sample may be divided for parallel analytical processes, and/or the sample can be delivered to one or more analyzers and/or racks. The pre-analytical phase 104 manages the flow of samples to different instruments and different analyzers within the lab system. This process management permits the system to operate efficiently and with minimal instruments. Additionally, the pre-analytical phase 104 ensures that a backup of patient samples at different points within the lab system does not occur along the process, or if a backup does occur, the pre-analytical phase 104 ensures that the backup can be cleared quickly and without significant impact on the remainder of the system.

Embodiments of the system can identify the patient samples as quickly as possible and determine the best scheduling of each sample to provide a consistent minimal turnaround time and maximum throughput of the analytical processes. The steps and organization of those steps in the process are designed to avoid backups of patient samples. Modules of the lab system can operate at a throughput speed that ensures processing of samples at the maximum throughput of the upstream processes. However, in some embodiments, at the aliquotter unit, the throughput may be managed by the introduction of samples upstream and by small queues at each aliquotter station.

Figure 2:
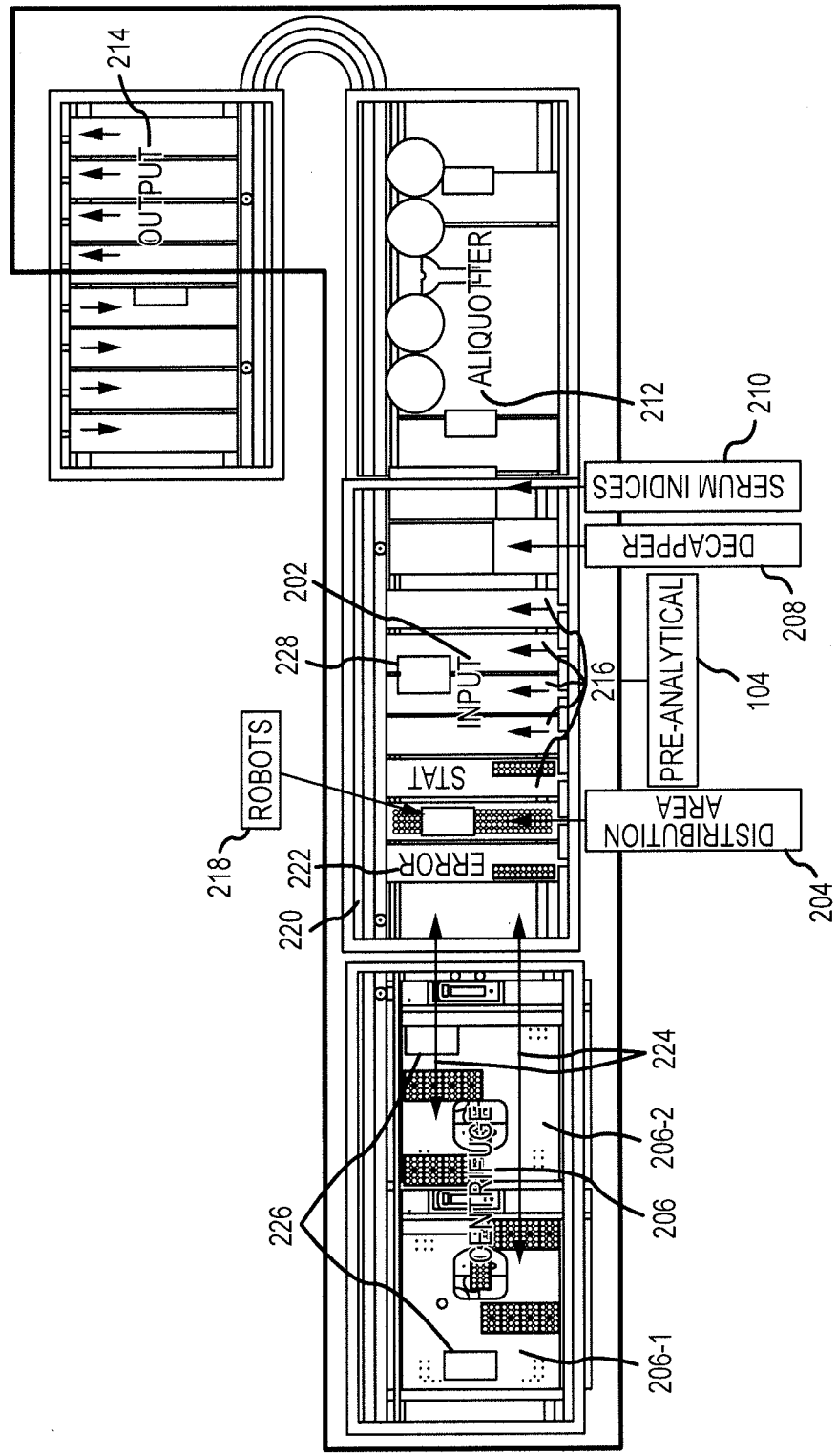
FIG. 2 shows a block diagram of components associated with a pre-analytical phase of a laboratory automation system.

FIG. 2 is a more detailed depiction of the components associated with the pre-analytical phase 104. The components associated with the pre-analytical phase 104 include seven modules: input module 202, distribution area 204, centrifuge module 206, decapper 208, serum indices measurement device 210, aliquotter 212, and output/sorter 214. Each of these modules may be physically and/or operationally coupled (directly or indirectly) to each other.

(a) Input Module

The input module 202 shown in FIG. 2 can accommodate a variety of tubes, racks, prioritizations, etc. and is capable of receiving a specimen. Racks of tubes and/or individual tubes can be loaded onto one of several lanes 216, which may be manually operated drawers and/or automated devices. In FIG. 2, five lanes 216 are depicted. However, the lab system can have any number of lanes 216. The lanes 216 are assigned priorities in accordance with those assigned by the user. In some embodiments, the highest priority lane (short turnaround time or "STAT") may have a fixed position for accepting a group of individual tubes from the user. Once tubes are loaded in the STAT lane, they become the next tubes processed. Other lanes can be assigned different priority levels in any manner. For example, when the drawers are manually operated, assigning one priority to at least two of the drawers and another priority to at least two other drawers may allow the system to operate continuously on one drawer while the other drawer of the same priority is available to the user.

In some embodiments, while the input module 202 is processing a drawer of samples, the user may be informed that the drawer should not be opened by using an indication such as a light on the drawer or a lock on the drawer. This may help maintain the process integrity and maximize throughput. When processing is complete on the first drawer, the drawer may be identified to the user as available, and the system may automatically begin processing another drawer. Additionally, the samples can be transferred to and from the drawers 216 of the input module 202 using an input module gripper 228.

(b) Distribution Area Module

From the lanes (or drawers) 216 within the input module 202 of FIG. 2, one of at least two or more grippers 218 (discussed in more detail below) may select the highest priority tube and transport it to a fixed matrix called the distribution area 204. The distribution area 204 is capable of distributing a specimen to a desired component of the laboratory automation system. During the transfer to this module by the input module gripper 228, the levels of the sample's constituent components are measured and photographs of the sample tube are taken. These photographs can be analyzed to determine the tube's manufacturer, diameter, height, cap color, etc. From this information, the volumes of the sample's components can be calculated, and an estimate of the total tube weight can be made. This weight can be later used to aid in balancing the centrifuge buckets in the centrifuge module 206, as will be discussed in more detail below.

To protect the distribution area 204 from filling with low priority tubes, a limit can be set on the number of tubes loaded into this area from the low priority input lanes. Moreover, the distribution area 204 may have a reserved area to ensure STAT samples have continuous access to the distribution area 204 from the STAT drawer in the input module 202.

The distribution area 204 can be the holding area which permits the system to access test information associated with the sample tube in the association phase 102 and plan the analysis process for the sample. This enables the system to schedule a sample tube's process with respect to the other sample tubes currently on the system. Scheduling enables the efficient processing of samples based upon priority without overloading any step in the overall system, permitting the optimization of turnaround time and throughput.

Furthermore, the sample's schedule can be updated throughout the process as the system's activity or availability changes, providing real time active control of the sample.

Once the schedule is planned by the distribution area module 204, a gripper 218 then selects the sample tube that is the next tube to be transferred to the next module based on the priority of the tubes within the distribution area 204. The selected sample tube is transported from the distribution area 204 to the conveyance system 220, to the centrifuge module 206, or to an output drawer with an error area 222 based on the analysis performed by the distribution area module 204.

If the sample tube is being moved to the centrifuge module 206, the tube can be placed into the appropriate centrifuge adapter based upon the earlier weight estimation to ensure proper balance of the centrifuge rotor. The centrifuge adapter is the component which carries the tubes upon a shuttle from the distribution area 204 to the centrifuge whereupon a robotic gripper transfers the centrifuge adapter with the tubes to a bucket of the centrifuge.

If the distribution area module 204 determines that the sample tube does not require centrifugation, the grippers 218 places the sample into a carrier on the conveyance system 220 with the barcode label properly aligned to the carrier at the direction of the scheduler so as not to overload downstream processes. More details on the conveyance system 220 and the carriers will be discussed below. A carrier can refer to any suitable device, which can be present in a conveyance system and can carry or transport one or more sample containers or tubes. Exemplary carriers may contain recesses which can hold the containers or tubes. If a problem exists with the sample (e.g., the volume is too low, the barcode is unreadable, no test information is downloaded, etc.), the sample tube is moved to the error area 222 and the user is notified of the issue.

(c) Centrifuge Module

The sample tube may be moved from the distribution area 204 of FIG. 2 to the centrifuge module 206 if the distribution area module 204 determines that the sample requires centrifugation before analysis of the sample. When a sample tube is to be transported from the distribution area 204 to the centrifuge module 206, the sample tube is loaded by the distribution area robot gripper 218 into a centrifuge adapter from the distribution area 204. The adapters may locate and retain multiple tube sizes for centrifugation. The adapter sits in a shuttle 224 which moves between the distribution area 204 and the centrifuge module 206 once the adapter is filled with sample tubes. An adapter can be a device which holds sample containers and can be used in a centrifuge. Such adapters are commonly constructed of a polymeric material but not limited to and constructed as a single piece having a shape which allows retention of one or more containers in which a sample may be placed. In some cases, an adapter is inserted into a device mounted on or in a centrifuge rotor. LabWare® (e.g., sample containers or tubes) holding the sample is inserted in the adapter.

When the sample tubes in the adapters arrive at the centrifuge module 206 from the distribution area 204 via the shuttle 224, the adapters are loaded into an available centrifuge bucket. The configuration of the adapters allows for simplification of delivery to and removal from the centrifugation buckets. Once loaded into a centrifuge bucket, the samples can be centrifuged. The centrifuge module 206 may include one or more centrifuges that are refrigerated to maintain the temperature of the sample. In FIG. 2, two centrifuges 206-1 and 206-2 are depicted. The centrifuges use a swinging centrifuge bucket rotor which produces level sedimentation layers from which analyzers and pipettors can consistently aspirate the maximum volume of fluid. Once centrifugation is complete, the adapters can be removed from the centrifugation bucket and placed in an unloading area. The sample tubes are then removed from the adapters in the unloading area and placed in carriers on the conveyance system 220 for transport to the next module.

The timing for loading tubes into an adapter at the distribution module 204, sending the tubes in the adapter to the centrifuge module 206 via the shuttle 224, loading the adapter into a centrifuge bucket, centrifuging the samples, unloading the adapter from the centrifuge bucket, and unloading the tubes from the adapter is such that the process can be continuous, allowing for the continual centrifugation of samples as they arrive at the centrifuge module 206 from the distribution area 204. As the centrifuge completes a spin cycle, the last tube in the distribution area 204 is loaded by the distribution area gripper 218 into an adapter, and the shuttle 224 moves the adapter to a centrifuge in the centrifuge module 206. At the same time, an automated door on the centrifuge opens and provides access to a bucket as the rotor indexes into position at the doorway. A centrifuge module gripper 226 in the centrifuge module 206 removes the adapter that is already in the bucket and moves the adapter to an area where the tubes will be unloaded to carriers on the conveyance system 220. Next, the centrifuge module gripper 226 selects an adapter that has been recently loaded with tubes from the distribution area 204 and deposits it into the empty bucket. While the rotor indexes to the next bucket, a previously emptied adapter is moved to the open position on the shuttle 224 for loading with tubes from the distribution area 204 when the shuttle 224 returns to the distribution area 204.

After the final adapter is loaded into the centrifuge, the door closes and the spin cycle begins. The adapter shuttle 224 moves back to the distribution area 204, and a centrifuge module gripper 226 begins to unload tubes from the adapters removed from the buckets into carriers on the conveyance system 220. As the tubes are moved from the adapter to the carrier, the heights of the sedimentation layers are measured and the barcode on each tube is aligned with the carrier. If insufficient serum or plasma is present, the tube will be sent to an error area located in the output module 214.

If the scheduling algorithm predicts the overloading of an analyzer with samples from the centrifuge module 206, the centrifuge module gripper 226 can unload the samples and distribute the samples from the adapters to the conveyance system. In some embodiments, the full cycle time of the centrifuges can be greater than or equal to, e.g., 360 seconds. In order to ensure optimal turnaround time (TAT) and throughput the centrifuges are kept, e.g., 180 seconds out of phase for a 360 seconds centrifugation cycle. In some embodiments, downstream processes do not prevent the unloading of samples from the centrifuge adapters. If all the remaining samples in an adapter are destined for unavailable process(es) and depending upon the unavailable process, sample tubes can either be moved to a buffer in the centrifuge instrument or moved to another buffer area elsewhere in the system.

The centrifuge module 206 may include an automated centrifuge controlled by a centrifuge controller. The automated centrifuge can be loaded with multiple centrifuge buckets or receptacles, each bucket receiving multiple sample tubes. The centrifuge includes a motor coupled to a spindle, a rotor assembly, a controller, a lid, and optionally, a lid drive. The centrifuge controller indexes or stops the spindle at selected positions for automated placement and removal of either tubes, adapters, or buckets. The lid has a closed position and an open position, and the lid opens and closes in response to instructions from the centrifuge controller.

In some embodiments, before the loaded buckets are placed in the centrifuge, the buckets can be balanced in a balance system. The balance system, which can be an included part of the centrifuge module 206, comprises a scale having sites for receiving and holding a plurality of buckets, and a balance controller for selectively depositing sample tubes in cavities of the buckets while correlating incremental weight changes with the locations of each deposit for equalizing weight in pairs of the buckets. The balance controller can be implemented as a balance program within the central controller. The balance program maintains a database of sample container weights. When a container's weight is combined with the sample's weight, the balance program can determine the optimum adapter cavity in which to place it thereby maintaining a balanced rotor within a tolerance. Sample weights are the product of density estimates and the sample volumes calculated from liquid level measurements and container geometry obtained during the initial pick-up from the input. In some embodiments, balance system may also include a supply of dummy loads in buckets for limiting weight variations between buckets. The dummy loads may be weighted for limiting the weight variations to not greater than, e.g., 10 grams between members of each pair of buckets.

In other embodiments, a scale need not be used. For example, in some embodiments, the weight of a sample container and a sample can be estimated, and the adapters can be automatically loaded to ensure a balanced rotor. In some cases, a picture of a sample tube may be taken, and the liquid level of a sample in the sample tube can be determined. Using information about the sample container (e.g., the sample container weight) and the determined liquid level, the weight of the sample tube with the sample in it can be estimated. In such embodiments, a scale is advantageously not needed. Further dummy loads may also not be needed.

The centrifuge controller may operate to perform a number of functions, such as receiving and storing a centrifuge spin profile including a rotor spindle speed and duration, indexing the rotor's sample stations into an access position, spinning the rotor in accordance with the cycle profile, stopping the rotor with a predetermined sample station at the access position, etc.

(d) Decapper Module

The decapper module 208 of FIG. 2 is capable of decapping the cap from the sample tubes in carriers on the conveyance system 220 before they are analyzed. The decapper system may clamp a sample tube and remove the cap from a sample tube. The decapper module 208 follows the distribution module 204 and the centrifuge module 206. For sample tubes which do not require cap removal (e.g., for instances in which the samples may only require sorting), the carrier on the conveyance system 220 will bypass the decapper module 208. For sample tubes that require cap removal, the decapper module 208 may remove the cap from the sample tube and deposit the cap in a biohazardous waste disposal container below the deck of the decapper module 208. The biohazardous waste disposal container is removable and replaceable to protect the user from biohazardous waste.

(e) Serum Indices Module

The serum indices module 210 of FIG. 2 is capable of measuring the serum index of a sample. Typically, this function is performed during the analytical phase 106. However, in some instances, certain laboratories may prefer to address any quality issues prior to delivering the samples to the analyzer. Thus, the serum indices module 210 provides this quality control option for samples that should be tested during the pre-analytical phase 104. For samples that do not require a serum index measurement, the sample may bypass the serum indices module 210.

The serum indices module 210 can be the next module after the decapper module 208 since a serum indices measurement typically requires access to the sample. Similar to the decapper module 208, the serum indices module 210 may have a biohazardous waste disposal container below the deck of this module. The container may be removable and replaceable to protect the user from biohazardous waste.

(f) Aliquotter Module

The aliquotter module 212 of FIG. 2 divides the sample in a primary tube into multiple secondary tubes depending on how many tubes are needed for analysis. This module may contain one or more pipettors for dividing the sample into secondary samples. Further details regarding the aliquotter module 212 can be found in U.S. Provisional Patent Application Nos. 61/556,667, filed Nov. 7, 2011, 61/616, 994, filed Mar. 28, 2012, and 61/680,066, filed Aug. 6, 2012.

3. Analytical Phase

Referring again to FIGS. 1 and 2, the analytical phase 106 includes performing the actual measurements needed to process a sample and produce results. This phase is typically composed predominantly of one or more analysis instruments or analyzers. The analysis instruments or analyzers can be any analysis instruments or analyzers known in the art. Typically, an analyzer may comprise a mechanism for selectively performing one or more types of analyses on a specimen. The analyzer's controller is in communication with the central controller, so that the central controller can instruct the analyzer controller as to what analysis to perform for the specimen. Each analyzer's controller may also communicate analysis results to the memory of the central controller.

For a laboratory system that has the components associated with the pre-analytical 104, analytical 106, and post-analytical 108 phases connected together via a conveyance system 220, the samples may move past the output/sorter module 214 and onto analyzers. When the carrier reaches the destination analyzer for that particular sample, the carrier pulls off the main travel lane and forms a queue upstream of the analyzer's access point to the conveyance system 220. The queue length is minimal because of the planning done by the scheduler while the tube was still in the distribution area 204 and because of the controlled release of tubes by the distribution 204 and centrifuge 206 modules.

B. Tube or Rack Presence Detection Unit

The laboratory automated system may use a tube or rack presence detection apparatus for detecting the presence of a sample tube or rack and its characteristics. Analysis tools or an image analysis device can be used to analyze or process one or more images acquired by one or more cameras and determine objects in the field of view of the cameras. The image analysis device can determine the presence and characteristics of each rack and of each sample tube in the rack and identify each sample tube in the rack using the determined characteristics.

The embodiments of the invention that relate to the tube or rack identification systems and methods can be used in any suitable part of the above-described system. For example, they may be used in the above-described input module 202, output module 214, or any other part of the system that uses racks and tubes.

In embodiments of the invention, as noted above, an "image acquisition device" may be used to capture images such as 2-D images of sample containers or sample container holders. Examples of image acquisition devices comprise cameras as well as detectors that can detect any suitable type of electromagnetic energy.

In embodiments of the invention, "sample container characteristics" may comprise any suitable characteristics about a sample container. Such characteristics may relate to a physical characteristic of a container such as a tube body and/or tube cap. Examples of sample tube characteristics include cap color, cap shape, labels and markers.

In embodiments of the invention, "sample container holder characteristics" may comprise any suitable characteristics of a sample holder. A sample container holder may include a number of recesses to hold an array of sample containers. Exemplary sample container holders characteristics may comprise any suitable characteristics including at least one of a size, shape, or color, as well as labels and/or markers that are associated with (e.g., on) the sample container holders.

1. Sample Tube or Rack Identification

Figure 3:
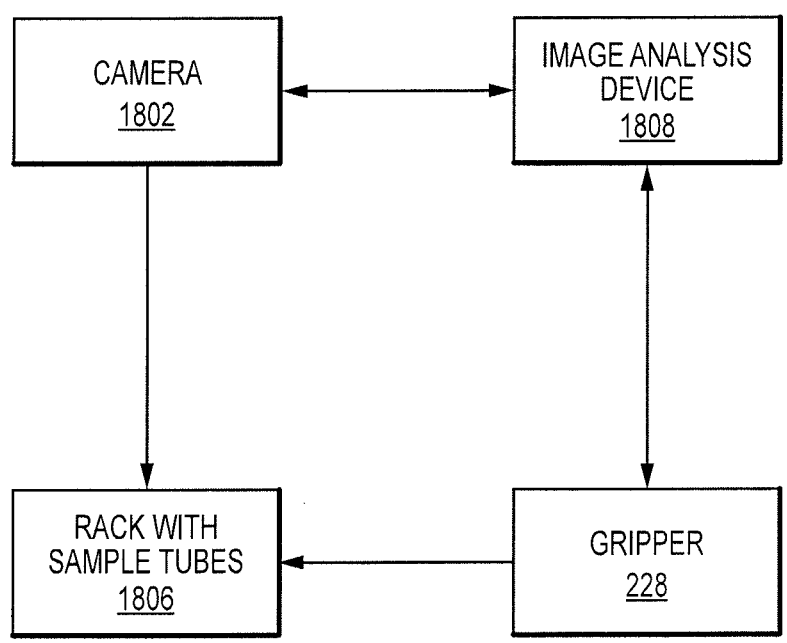
FIG. 3 shows a system diagram according to an embodiment of the invention.

FIG. 3 shows a high-level block diagram of some components in a sample tube and rack identification system according to an embodiment of the invention. FIG. 3 shows a camera 1802 coupled to an image analysis device 1808. The image analysis device 1808 can also be coupled to a gripper 228 and can provide instructions to it. The gripper 228 can then secure a specific sample tube in a rack with sample tubes 1806(*a*).

Although the instructions provided by the image analysis device are provided to a gripper 228 in this example, embodiments of the invention are not limited thereto. For example, embodiments of the invention can provide instructions to a central controller in the laboratory automation system to inform other downstream instruments or subsystems that a particular tube and/or rack has been identified. For example, once a particular sample tube in a sample rack has been identified, a scheduler in a central controller will know where that particular sample tube is in the system and can plan ahead for any subsequent processing. Thus, the instructions and/or analysis data provided by the image analysis device 1808 may be provided to any suitable downstream instrument or subsystem.

Figure 4:
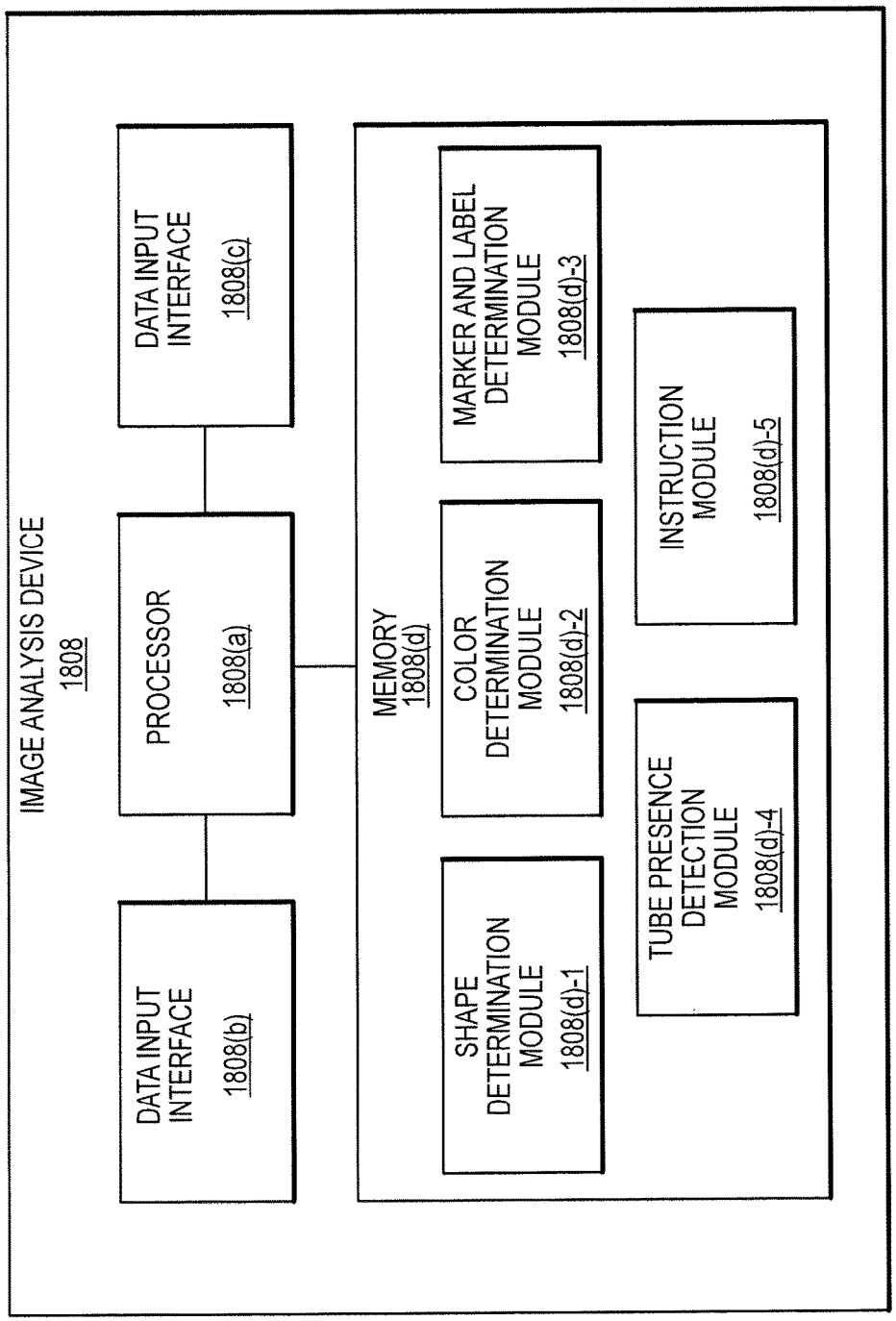
FIG. 4 shows a high-level block diagram of a tube and rack identification system showing elements of an analysis device according to an embodiment of the invention.

FIG. 4 shows a block diagram of an image analysis device 1808. It may include a data input interface 1808(*b*) to receive data from the one or more cameras (e.g. camera 1802), and a processor 1808(*a*) coupled to the input interface 1808(*b*). The processor 1808(*a*) may also be coupled to a data output interface 1808(*c*) which provides data to suitable devices which can manipulate and/or transport a sample tube. The central processor 1808(*a*) may further be coupled to a memory 1808(*d*) which may comprise shape determination module 1808(*d*)-1, a color determination module 1808(*d*)-2, a marker and label determination module 1808(*d*)-3, a tube presence detection module 1808(*d*)-4, and an instruction module 1808(*d*)-5. The shape determination module 1808(*d*)-1 may comprises computer code, executable by the processor 1808(*a*), to determine the shape of a sample tube or rack. The color determination module 1808(*d*)-2 may comprise computer code, executable by the processor 1808(*a*) to determine a color of a sample tube cap or rack. The marker and label determination module 1808(*d*)-3 may comprise computer code, executable by the processor 1808(*a*) to determine marker or label associated with a cap, tube body, or rack. The tube presence detection module 1808(*d*)-4 may comprise code, executable by the processor, to determine the absence or presence of a sample tube at a particular rack location within a rack. The sample tube instruction module 1808(*d*)-5 may comprise code, executable by the processor 1808(*a*) to provide instructions to an external device via the data output interface 1808(*c*). The instructions that are provided may include instructions to a gripper unit, which cause the gripper unit to locate and grip a particular sample tube or tubes in one or more racks. Note that any of the previously described software modules may function independently or together. For instance, the shape determination module 1808(*d*)-1 may operate with the color determination module 1808(*d*)-2 to identify both the shape of a particular cap as well as its color, in order to identify the sample tube associated with the cap.

In methods according to embodiments of the invention, at least one camera acquires at least one image of the rack with sample tubes comprising samples. The method further comprises analyzing, by the image analysis device, the at least one image to identify characteristics of the sample tubes and/or rack. If the sample tubes comprise different samples, then these samples may be in different sample tubes with different characteristics, and the samples may be processed differently, after they have been identified. For example, after receiving instructions from the analysis device, a first sample tube with a first characteristic and a first sample could be sent to a storage unit by a gripper (coupled to a robotic arm) that is capable of moving in three directions (X, Y, and Z), while a second sample tube with a second characteristic and a second sample may be sent to a centrifuge, prior to being analyzed.

The processor 1808(*a*) may comprise any suitable data processor for processing data. For example, the processor may comprise one or more microprocessors that function separately or together to cause various components of the system to operate.

The memory 1808(*d*) may comprise any suitable type of memory device, in any suitable combination. The memory 1808(*d*) may comprise one or more volatile or non-volatile memory devices, which operate using any suitable electrical, magnetic, and/or optical data storage technology.

FIG. 5(*a*) shows a system 1800 comprising a camera unit (e.g., 2-D arrays or line scanners) comprising a camera 1802 and illumination elements 1804 (e.g., lights). The camera 1802 acquires a 2-D image for a target object can be used in the laboratory automation system to detect the presence of and identify the target object. The camera 1802 and the illumination elements 1804 may be movable or stationary and may be mounted to a frame (not shown) in a processing module above racks with sample tubes. In this example, the target objects are multiple sample tubes 1806(*a*) being provided in a 6×6 rack 1806(*b*). The 2-D image can then be further processed by image analysis software in the image analysis device and can detect the presence and to derive characteristics of the target object (e.g., sample tubes or racks), such as tube cap indicators, rack markers, circular barcode labels, cap or rack color and shape, etc. The 2-D image can also be analyzed to determine the presence or absence of a sample tube in various sample tube locations in the rack 1806. By analyzing the tube characteristics and by analyzing the presence of the sample tubes in a rack, a gripper or other transport device knows which samples to select for further processing, and also knows whether or not additional samples can be placed in the rack for further processing.

Figure 5C:
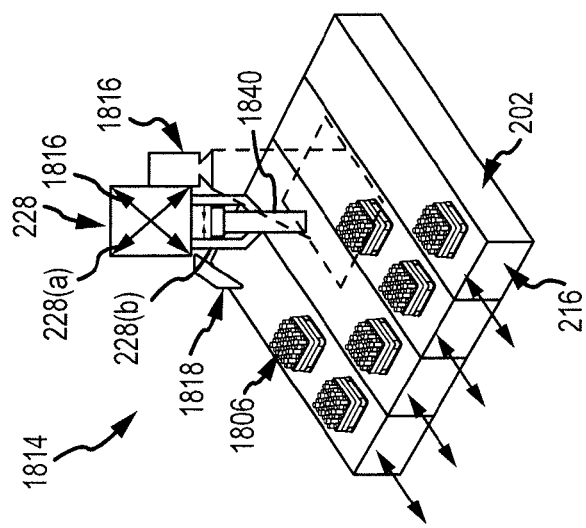
FIGS. 5(a)-5(c) show examples of camera units for sample tube or rack detection and analysis.
Figure 5B:
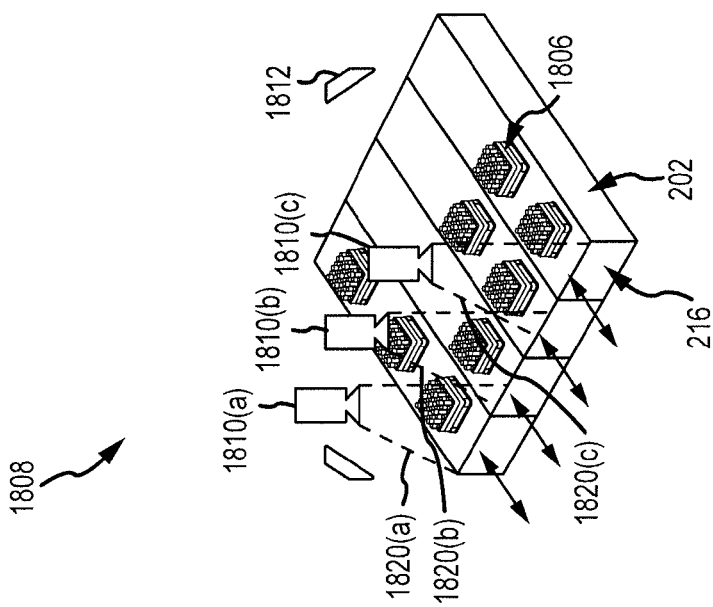

FIG. 5(b) depicts another embodiment of a system for sample tube or rack detection and analysis. The image analysis device 1808 (e.g., camera unit, 2-D arrays or line scanners) comprises a plurality of cameras 1810(a), 1810(b), 1810(c) and illumination elements 1812 to acquire one or more 2-D images of the target objects can be used in the laboratory automation system to detect the presence of and identify the target objects. The image analysis device 1808 comprising the plurality of cameras 1810(a), 1810(b), 1810 (c) is arranged on top of an input module 202 facing the input area including the target objects. In this example, the target objects comprise sample tubes being provided in racks 1806 provided on a plurality of parallel drawers 216 of the input module 202. As shown, the plurality of cameras 1810(a), 1810(b), 1810(c) can capture different images 1820(a), 1820(b), 1820(c). Adjacent images 1820(a), 1820 (b) and 1820(b), 1820(c) can overlap so a larger image can be stitched together if desired.

The 2-D images obtained by the plurality of cameras 1810(a), 1810(b), 1810(c) can then be further processed by image analysis software to detect the presence of and to derive characteristic features of the target objects (e.g., sample tubes and racks), such as tube cap indicators, rack markers, circular barcode labels, cap or rack color and shape, etc. Either a series of images can be acquired by the image analysis device 1808 during the movement of the drawers 216, or an overview image of the input area can be made in a closed state for the drawers 216.

FIG. 5(c) depicts another embodiment of a camera unit for sample tube or rack detection and analysis. A camera unit 1814 (e.g., 2-D arrays or line scanners) having a camera 1816 and illumination elements 1818 to acquire 2-D images for target objects can be used in the laboratory automation system to detect the presence of and identify the target objects.

The camera unit 1814 is coupled to a lower end of a gripper 228 facing the input area. The gripper 228 comprises a gripper body 228(a) and gripper fingers 228(b), which can grip a sample tube 1840. The gripper 228 may also be attached to an X-Y gantry 1817 so that the gripper 228 can move in an X, Y, or Z direction. A series of images is acquired by the camera 1816 during the movement of the input gripper 228.

In this example, the target objects are one or more sample tubes being provided in one or more racks 1806 provided on the drawers 216 of the input unit 202. The 2-D image can then be further processed by image analysis software to derive characteristic features of the target object (e.g., sample tubes and racks), such as tube cap indicators, rack markers, circular barcode labels, cap or rack color and shape, etc.

When the camera unit 1814 takes a series of images, the images can be stitched together by the analysis tool to generate an overview image. Within this overview image, single objects can be detected by image analysis performed by the analysis tool. For example, single objects such as markers on the holding racks or a cap or closure of a sample tube located in a holding rack can be detected using image analysis.

The embodiment in FIG. 5(c) has advantages. For example, using this embodiment, a image can be taken of a sample tube rack with samples, and the image can be analyzed, and the gripper can be instructed to select the appropriate sample tube from the sample tube rack and/or place a tube in a vacant sample tube location in the rack. The gripper and its robotic arm and process information while it is moving, thereby resulting in a very efficient process.

Figure 6:
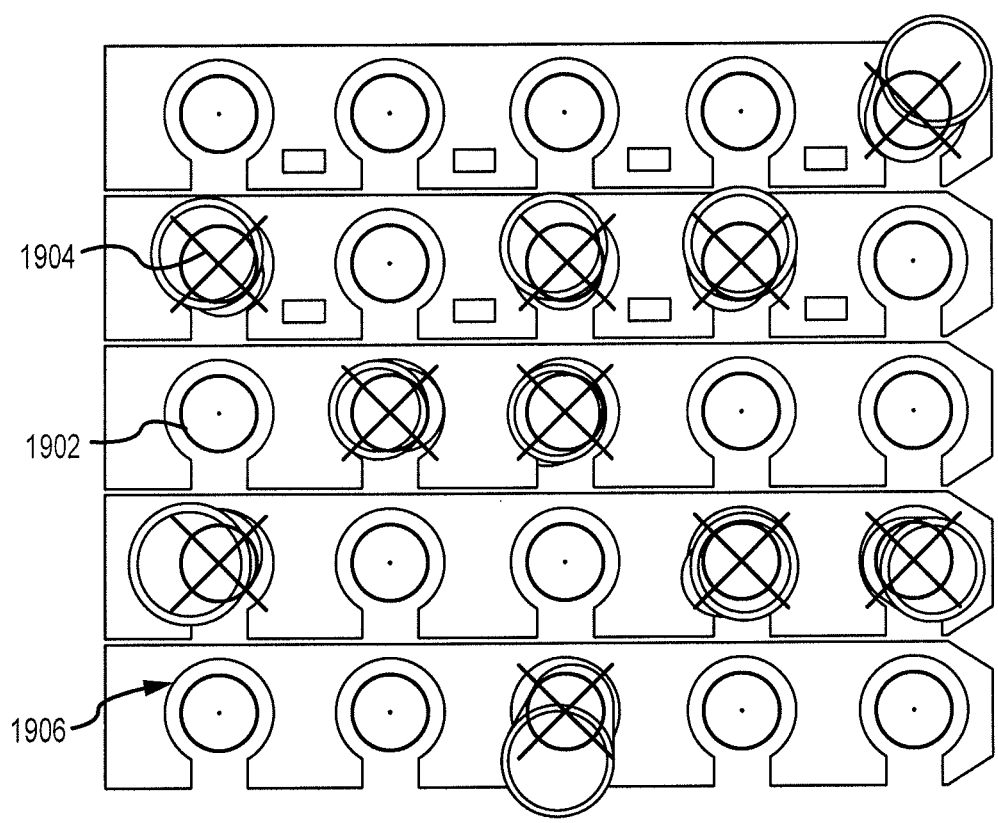
FIG. 6 show an example of an original image and a resulting analyzed image of a rack with sample tubes after a presence detection analysis.

FIG. 6 depicts an example overlay image of an original image and the highlighted analyzed image of the sample tube identification in a sample rack based on a top-view image. Detected potential positions for a sample tube are highlighted with circles 1902, while a detected sample tube is indicated by a cross 1904. Shape recognition software can recognize outlines of potential locations for sample tubes by recognition of particular shapes for the recesses that can receive the sample tubes. In some cases, the recesses in the rack may be colored to assist in the recognition of the empty recesses. Other rack locations with sample tubes cover the empty recesses, and may therefore be considered to be filled with sample tubes. A map of circles and crosses can be formed as shown in FIG. 6, and this can be overlaid on a top plan view image of the rack with the tubes. In some cases, the particular characteristics of the rack and the locations for sample tube placement (e.g., recesses) can be previously mapped and stored in a memory in the system. Thus, embodiments of the invention may determine the presence and/or absence of a sample tube at a particular rack location in a rack.

The analysis tool according to an embodiment of the invention is also capable of deriving details such as cap color, cap shape, markers or labels on the cap for a single sample tube in a holding rack, etc. The derived details may then be used to optimize the subsequent process steps for the laboratory automated system.

2. Sample Tube Marker (a) Urgent Sample Indicator

The laboratory automation system can utilize a sample status indicator device, which can provide an easy way to mark a sample tube as an emergency or urgent tube requiring immediate analysis, without the application of additional material on the sample tube. Currently, sample tubes may be marked with self-adhering labels (e.g., colored labels indicating urgency), "urgent" stickers, or just by using a handwritten note indicating urgency on already existing labels. The urgent sample indicator mechanism of the present technology can indicate urgency or status of the sample without the need to label or handwrite the indication.

The sample status indicator device includes a manually moveable element of the sample tube cap, wherein the moveable element can be moved to at least a first position and a second position. When the moveable element is moved to a first position, a window may display a first status of the sample tube (e.g., normal or non-urgent). When the moveable element is moved to a second position, the window may display a second status of the sample tube (e.g., a mark indicating an urgent status). The indicator or marker can be read by operators as well as by an automated system. The indicator or marker can be a particular color, characters, numbers, icons, etc.

For example, as soon as tubes with different priorities get collected in a multiple-tube rack, the conventional labels may get covered by the rack itself of by neighbor tubes, thus making it difficult to recognize such labels or stickers as an emergency mark for automated processes. In conventional situations, presorting must typically be performed. The urgent sample indicator of the present technology can provide the visual marker on the top of the tube so that the urgent tubes can be recognized immediately by users as well as by an automated process via image processing. This allows the user to mix emergency samples together with lower priority samples in a rack or bag for transport. Undetected emergency samples become unlikely, and additional presorting may not be required.

The indicators in embodiments of the invention can be status indicators. Examples of particular tube statuses include, but are not limited to, the particular priority associated with a tube (e.g., urgent, not urgent, STAT, etc.), the particular processing desired for a tube (e.g. centrifuge, aliquot, etc.), etc.

In one embodiment, the markers are not limited to emergency or prioritization marking, and can alternatively allow for several visual predefined marks, such as container content material, additives, reagents, etc., without the need for different parts. The moveable element can be moved (e.g., a first direction or second direction) to a certain position so that the window displays a particular indicator.

In one embodiment, the positions to which the moveable element can be moved may have a mechanical latch function or a limitation device to switch between two or more positions. This prevents the moveable part from being accidentally moved to an incorrect position.

Figure 7:
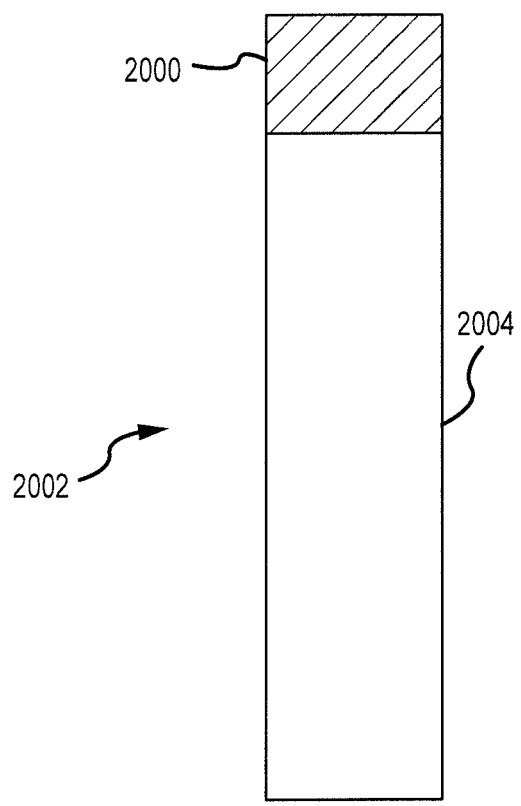
FIG. 7 shows a sample tube with a sample tube body and a sample tube cap.

FIG. 7 shows a view of a sample tube 2002 comprising a sample tube body 2004 and a cap 2000 on the sample tube body. A sample such as a biological sample can be present in the sample tube 2002. The sample tube body 2004 may comprise a transparent or translucent material comprising plastic or glass. The sample cap 2000 may also comprise a material such as plastic.

FIGS. 8(a)-8(b) depict one example of a cap 2000 having a movable element that expose or not expose an urgent sample indicator.

In FIG. 8(a), the cap 2000 comprises a cylindrical cap body 2000(a) and a movable element 2000(b) at a top region of the cylindrical cap body 2000(a). The movable element 2000(b) may rotate so that a window 2000(b)-1 exposes a non-urgent indicator 2004. The non-urgent indicator 2004 may be a color such as green to indicate that the sample is to be processed in a non-urgent manner. Handles 2000(b)-2 in the form of protrusions may be present in the movable element 2000(b) to allow a human, a gripper or other element to move the movable element 2000(b) change the status of the sample tub. While handles are described in detail, embodiments of the invention can include other types of handling features such as holes.

In FIG. 8(b), the movable element 2000(b) is rotated an emergency or urgent position to expose an urgent sample indicator 2005. The urgent sample indicator 2005 may be red to indicate that the sample tube is to be processed as soon as possible.

While the indicators in FIGS. 8(a) and 8(b) are non-urgent 2004 and urgent 2005, respectively, it is understood that the sample tube cap 2000 shown in FIGS. 8(a) and 8(b) could have other types of indicators. For example, the indicators may indicate that a sample is to be processed by a particular machine, by a particular process, in a particular order, etc.

Figure 5A:
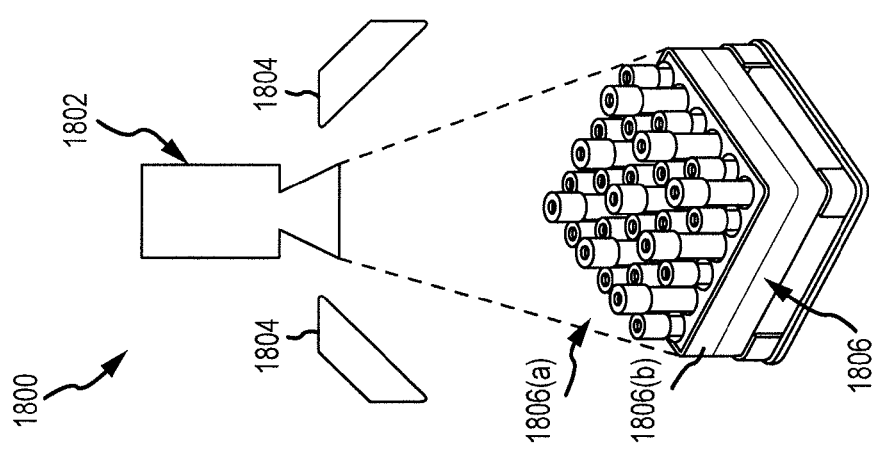

The cap 2000 and its indication of sample tube status can be viewed by the camera units shown in FIGS. 5(a)-5(c) and can be identified and processed as described above.

(b) Centrifugation Indicator

The laboratory automation system can utilize a centrifugation status indicator device, which can indicate whether a sample has been centrifuged. Generally, the majority of sample tubes in a lab require centrifugation since only their serum is used for analysis. When a sample tube sits for long period of time, there is sedimentation of the specimen so that the specimen appears visually to have been spun. Additionally, it could become less apparent that a pre-spun sample was actually already spun if the specimen were shaken (e.g., during transport). If sample tubes that have been sitting for a period of time and pre-spun sample tubes are mixed, a user may not be able to discern which samples tubes were actually already spun. Furthermore, it may be difficult for a user to visually determine the quality of the centrifugation (e.g., whether or not the spin time and force (minutes*g) was sufficient or not).

The centrifugation status indicator device of the present technology provides a way to visualize the centrifugation status of a sample tube. The centrifugation status can be read by users or by a lab automation device independent from the actual appearance of the blood or other specimen in the sample tube. The centrifugation indicator prevents user error which could result in incorrect test results. The centrifugation indicator provides a visual mark which changes its appearance during centrifugation according to the centrifugation time and force, but keeps its state under normal tube transport conditions.

The visual marker of the centrifugation indicator may be on the top of the sample tube so that it can be recognized immediately by users as well as by an automated process via image processing. It allows pre-spun samples to be mixed with un-spun samples in a rack and avoids the manual presorting of samples prior to automation entry. In one embodiment, the centrifuge indicator can be part of the sample tube cap for covering the sample tube.

Additionally, the centrifugation quality can be determined automatically and subsequent processes in the laboratory automation system can be controlled according to the result. One embodiment of a centrifugation indicator is shown in FIG. 9(a). The centrifugation indicator depicted includes a small container (which may be in the form of a cap housing) with a transparent top containing a colored gel 2302 (e.g. white) and particles 2304 of a different (e.g., higher) density and with a different color (e.g., blue). In an unspun state 2104, the particles 2304 and the colored get 2302 are distinct from each other. Using the example of white gel 2302 and blue particles 2304, the initial appearance of the container may be light blue when the two components are initially mixed, or the appearance may be blue in case the particles are on top of the gel 2302. During centrifugation, the blue particles move to the bottom of the container due to the higher density 2308, and the top appearance changes to white due to the lack of particles 2310. The combination of the chosen materials provides the possibility to gain different appearances according to the applied centrifugation force and time. Additionally, more than one type of particles can be used to get a finer resolution of the applied spin time and force.

In one embodiment, the centrifugation indicator is a transparent cylinder that is pressed onto a pressure sensitive device (e.g., pressure indicating film) which changes its appearance according to the applied centrifugation force. FIG. 9(b) depicts an example of this type of centrifugation indicator. The centrifugation indicator includes the pressure sensitive device 2312 (e.g., foil) in a transparent cylinder 2314, which may comprise a transparent material such as a transparent gel. The transparent cylinder 2314 allows the pressure sensitive device 2312 to be displayed. When the sample is not spun 2316, the pressure sensitive device 2312 may have a transparent appearance. During centrifugation 2318, the pressure sensitive device 2312 on the centrifugation indicator may have an appearance of one particular color. Once the sample tube has been spun 2320, the pressure sensitive device 2312 on the centrifugation indicator may have another appearance of another particular color. One example of a pressure sensitive device 2312 may be Prescale™ film by Fujifilm®.

Figure 10A:
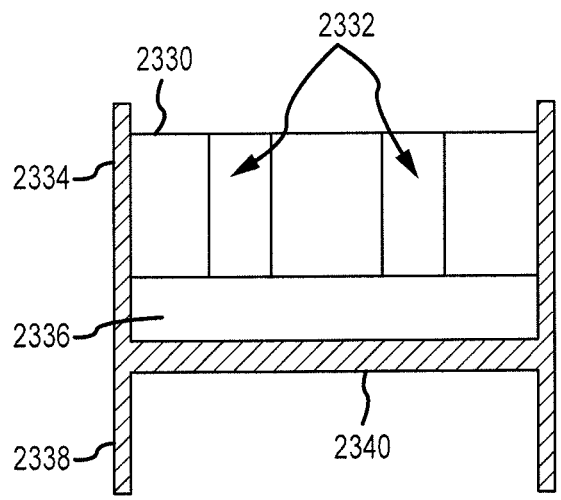
FIGS. 10(a)-10(b) show a non-centrifuged cap embodiment from a side cross-sectional view and a top plan view, respectively.
Figure 10B:
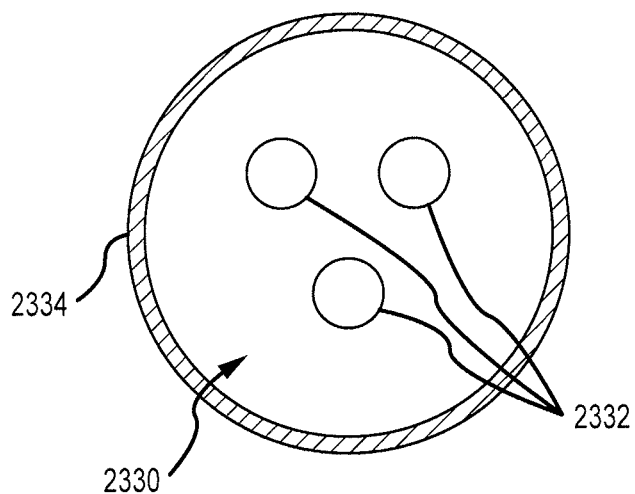

FIG. 10(*a*) shows a side, cross-sectional view of a cap with a pressure sensitive device 2336 in the form of a foil. The cap is shown in a non-centrifuged state. As shown, the cap can include a body with a cylindrical cap thread portion 2338 and a cylindrical cap top portion 2334 separated by a perpendicular circular horizontal portion 2340. A pressure sensitive device 2336 is on the horizontal portion 2340. A plurality of transparent posts 2332 may be on the pressure sensitive device 2336, and the top surfaces of the posts 2332 may be covered with an optically transparent cover 2330 (e.g., made of transparent plastic).

FIG. 10(*b*) shows a top plan view of the cap in FIG. 10(*a*). In FIGS. 10(*a*) and 10(*b*), like reference numbers designated like elements. As shown, the pressure sensitive device 2336 may be a first color when no pressure is applied to it.

Figure 11A:
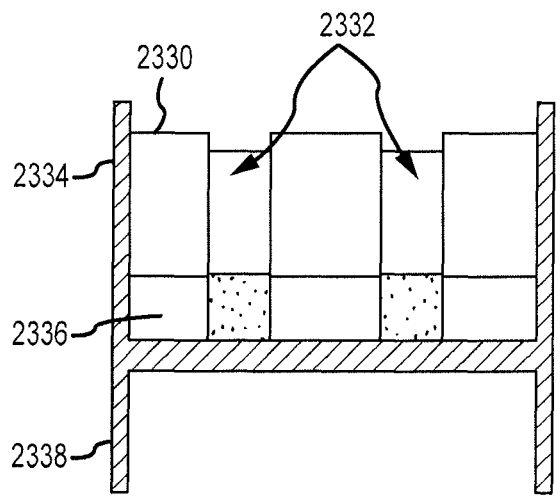
FIGS. 11(a)-11(b) show a centrifuged cap embodiment from a side cross-sectional view and a top plan view, respectively.
Figure 11B:
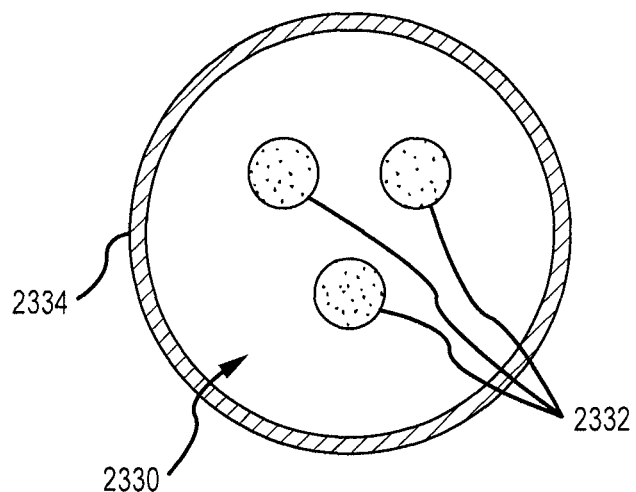

The same cap is shown in FIGS. 11(*a*) and 11(*b*). However, this cap is shown after centrifugation. As shown, the posts 2332 applied downward pressure on the pressure sensitive device 2336 causing a color change in the pressure sensitive device 2336 at areas under the posts 2332. When viewed from the top in FIG. 11(*b*), a distinct pattern of three dots (of a second color) is shown against a background of a different color (e.g., the first color). This pattern can be viewed by a camera looking down on the cap, and an analysis device coupled to the camera can determine that the sample tube with the cap contains a centrifuged sample (as described above with respect to FIGS. 5(*a*)-5(*c*).

(c) Circular Barcode

The laboratory automation system can utilize a circular barcode identification device on top of a sample tube cap. A circular barcode can provide for an easy and fast way to identify the sample tubes before they get handled by the input gripper for the first time.

The various participants and elements described herein with reference to the figures may operate one or more computer apparatuses to facilitate the functions described herein. Any of the elements in the above description, including any servers, processors, or databases, may use any suitable number of subsystems to facilitate the functions described herein, such as, e.g., functions for operating and/or controlling the functional units and modules of the laboratory automation system, transportation systems, the scheduler, the central controller, local controllers, etc.

Figure 12:
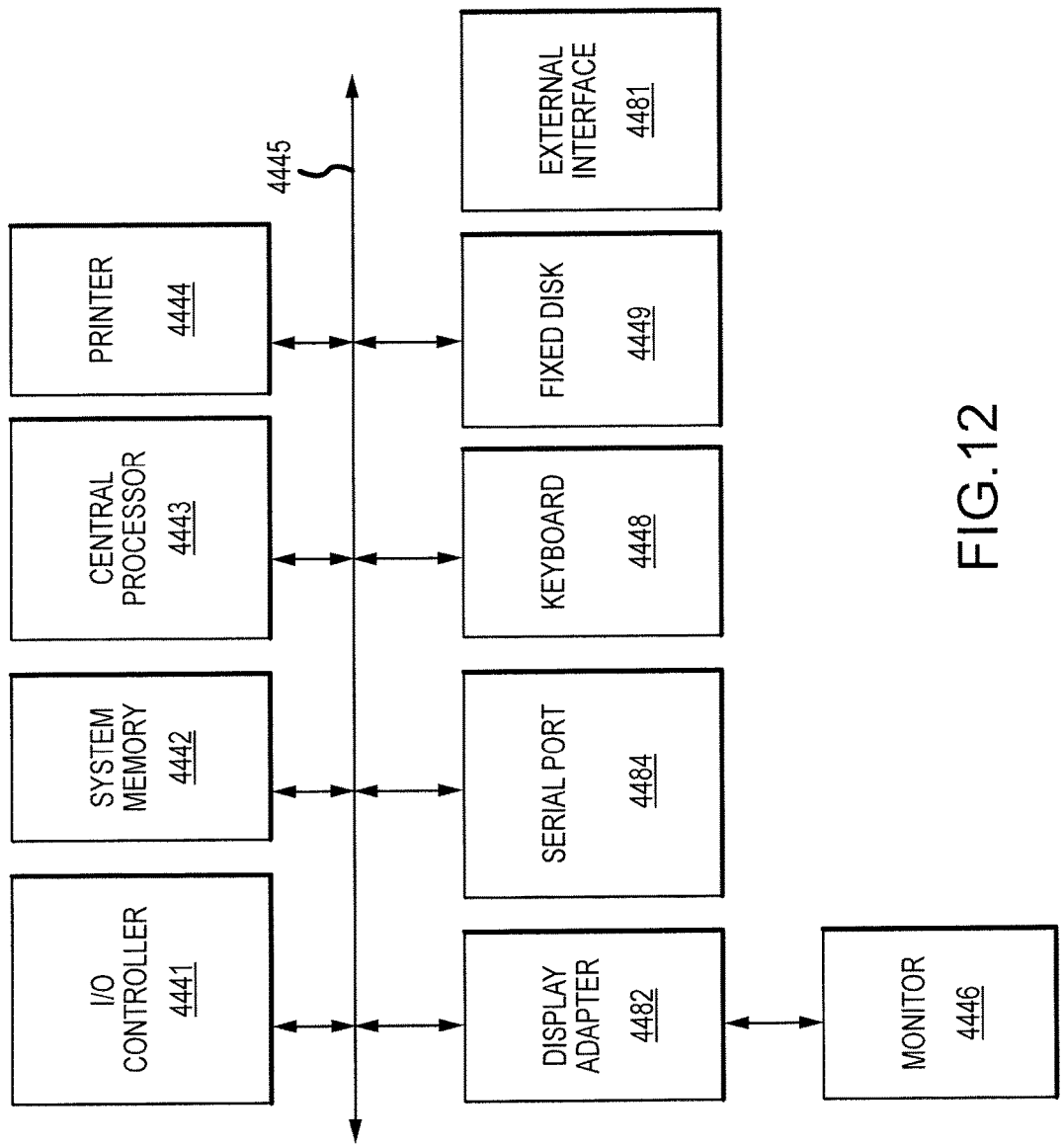
FIG. 12 show a block diagram of an exemplary computer apparatus.

Examples of such subsystems or components are shown in FIG. 12. The subsystems shown in FIG. 12 are interconnected via a system bus 4445. Additional subsystems such as a printer 4444, keyboard 4448, fixed disk 4449 (or other memory comprising computer readable media), monitor 4446, which is coupled to display adapter 4482, and others are shown. Peripherals and input/output (I/O) devices, which couple to I/O controller 4441 (which can be a processor or other suitable controller), can be connected to the computer system by any number of means known in the art, such as serial port 4484. For example, serial port 4484 or external interface 4481 can be used to connect the computer apparatus to a wide area network such as the Internet, a mouse input device, or a scanner. The interconnection via system bus allows the central processor 4443 to communicate with each subsystem and to control the execution of instructions from system memory 4442 or the fixed disk 4449, as well as the exchange of information between subsystems. The system memory 4442 and/or the fixed disk 4449 may embody a computer readable medium.

Embodiments of the technology are not limited to the above-described embodiments. Specific details regarding some of the above-described aspects are provided above. The specific details of the specific aspects may be combined in any suitable manner without departing from the spirit and scope of embodiments of the technology. For example, back end processing, data analysis, data collection, and other processes may all be combined in some embodiments of the technology. However, other embodiments of the technology may be directed to specific embodiments relating to each individual aspect, or specific combinations of these individual aspects.

It should be understood that the present technology as described above can be implemented in the form of control logic using computer software (stored in a tangible physical medium) in a modular or integrated manner. Furthermore, the present technology may be implemented in the form and/or combination of any image processing. Based on the disclosure and teachings provided herein, a person of ordinary skill in the art will know and appreciate other ways and/or methods to implement the present technology using hardware and a combination of hardware and software.

Any of the software components or functions described in this application, may be implemented as software code to be executed by a processor using any suitable computer language such as, for example, Java, C++ or Perl using, for example, conventional or object-oriented techniques. The software code may be stored as a series of instructions, or commands on a computer readable medium, such as a random access memory (RAM), a read only memory (ROM), a magnetic medium such as a hard-drive or a floppy disk, or an optical medium such as a CD-ROM. Any such computer readable medium may reside on or within a single computational apparatus, and may be present on or within different computational apparatuses within a system or network.

The above description is illustrative and is not restrictive. Many variations of the technology will become apparent to those skilled in the art upon review of the disclosure. The scope of the technology should, therefore, be determined not with reference to the above description, but instead should be determined with reference to the pending claims along with their full scope or equivalents.

One or more features from any embodiment may be combined with one or more features of any other embodiment without departing from the scope of the technology.

A recitation of "a", "an" or "the" is intended to mean "one or more" unless specifically indicated to the contrary.

All patents, patent applications, publications, and descriptions mentioned above are herein incorporated by reference in their entirety for all purposes. None is admitted to be prior art.

What is claimed is:

1. A sample container cap comprising:
   a sample cap body capable of covering an opening of a sample container; and
   a centrifugation status indicator device in the top of the sample cap body, wherein the centrifugation status indicator device comprises:
      a first substance having a first density and a first color, wherein the first substance comprises a gel; and
      a second substance having a second density and a second color, wherein the second substance comprises a plurality of particles, wherein the second density is higher than the first density and wherein the second color is different from the first color, and wherein the centrifugation status indicator device displays the first substance when the sample container has been centrifuged.

2. The sample container cap of claim 1, wherein the first and second substances are combined after centrifugation but are not combined without centrifugation.

3. The sample container cap of claim 1 wherein the centrifugation status indicator device comprises a combination of materials that change appearance according to applied centrifugation force and time.

4. The sample container cap of claim 1 wherein the sample cap body is transparent.

5. The sample container cap of claim 4 wherein the sample cap body is cylindrical.

6. The sample container cap of claim 4 wherein the sample cap body comprises a cap thread portion.

7. The sample container cap of claim 1 wherein the sample cap body includes a cylindrical cap thread portion and a cylindrical cap top portion, separated by a circular portion.

8. A sample container cap comprising:
a sample cap body capable of covering an opening of a sample container; and
a centrifugation status indicator device in the top of the sample cap body, wherein the centrifugation status indicator device comprises a pressure sensitive device extending in a first direction and transparent cylindrical elements that contact the pressure sensitive device and that extend perpendicular to the first direction of the pressure sensitive device, wherein the transparent cylindrical elements are configured to press onto the pressure sensitive device during centrifugation.

9. The sample container cap of claim 8 wherein the pressure sensitive device comprises a foil configured to change appearance in response to applied pressure.

10. The sample container cap of claim 9 wherein the foil is configured to change color in response to applied pressure.

11. The sample container cap of claim 8 wherein the pressure sensitive device comprises a pressure sensitive foil.

12. A method comprising:
attaching a sample container cap comprising a sample cap body, and a centrifugation status indicator device in the top of the sample cap body, to a sample container body containing a sample; and
centrifuging the sample in the sample container body, wherein the centrifugation status indicator indicates a status of centrifugation, wherein the centrifugation status indicator device comprises:
a first substance having a first density and a first color, wherein the first substance comprises a gel; and
a second substance having a second density and a second color, wherein the second substance comprises a plurality of particles, wherein the second density is higher than the first density and wherein the second color is different from the first color, and wherein the centrifugation status indicator device displays the first substance when the sample container has been centrifuged.

13. The method of claim 12, wherein the centrifugation status indicator device comprises a combination of materials that change appearance according to applied centrifugation force and time.

14. The method of claim 12, wherein the sample cap body is transparent.

15. The method of claim 12, wherein the sample cap body comprises a cap thread portion.

16. A method comprising:
attaching a sample container cap comprising a sample cap body, and a centrifugation status indicator device in the top of the sample cap body, to a sample container body containing a sample; and
centrifuging the sample in the sample container body, wherein the centrifugation status indicator indicates a status of centrifugation, wherein the centrifugation status indicator device comprises a pressure sensitive device and transparent cylindrical elements that are perpendicular to the pressure sensitive device and contact the pressure sensitive device, wherein the transparent cylindrical elements press onto the pressure sensitive device during centrifuging the sample.

17. The method of claim 16 wherein the pressure sensitive device comprises a foil configured to change appearance in response to applied pressure.

* * * * *